(12) United States Patent
Backus

(10) Patent No.: US 10,974,048 B2
(45) Date of Patent: Apr. 13, 2021

(54) COCHLEAR IMPLANT SYSTEM FOR PROCESSING MULTIPLE SOUND SOURCE INFORMATION

(71) Applicant: Oticon Medical A/S, Smørum (DK)

(72) Inventor: Bradford Backus, Vallauris (FR)

(73) Assignee: Oticon Medical A/S, Smørum (DK)

( * ) Notice: Subject to any disclaimer, the term of this patent is extended or adjusted under 35 U.S.C. 154(b) by 222 days.

(21) Appl. No.: 15/806,753

(22) Filed: Nov. 8, 2017

(65) Prior Publication Data

US 2018/0133477 A1    May 17, 2018

(30) Foreign Application Priority Data

Nov. 11, 2016  (EP) .................................... 16198413

(51) Int. Cl.
  *A61N 1/36*   (2006.01)
  *A61N 1/05*   (2006.01)
  *H04R 25/00*  (2006.01)

(52) U.S. Cl.
  CPC ....... *A61N 1/36038* (2017.08); *A61N 1/0541* (2013.01); *A61N 1/36036* (2017.08);
  (Continued)

(58) Field of Classification Search
  CPC ............ A61N 1/36036; A61N 1/36038; A61N 1/0541
  See application file for complete search history.

(56) References Cited

U.S. PATENT DOCUMENTS

| | | | | |
|---|---|---|---|---|
| 2005/0107843 A1* | 5/2005 | McDermott | ....... | A61N 1/36036 607/57 |
| 2006/0265061 A1 | 11/2006 | Kwon et al. | | |

(Continued)

FOREIGN PATENT DOCUMENTS

| | | |
|---|---|---|
| EP | 2 192 794 A1 | 6/2010 |
| EP | 2 563 045 A1 | 2/2013 |

(Continued)

OTHER PUBLICATIONS

Taft et al., "Across-Frequency Delays Based on the Cochlear Traveling Wave: Enhanced Speech Presentation for Cochlear Implants", IEE Transactions on Biomedical Engineering vol. 57 No. 3, Mar. 2010, pp. 596-606.

*Primary Examiner* — Michael J D Abreu
(74) *Attorney, Agent, or Firm* — Birch, Stewart, Kolasch & Birch, LLP

(57) ABSTRACT

According to an embodiment, a cochlear implant system is disclosed. The system includes an input unit, a filterbank, a processing unit and an implant. The input unit is configured to provide a first electrical signal from a first sound source and a second electrical signal from a second sound source. The filterbank is configured to filter the first electrical signal into a plurality of first band limited signals and the second electrical signal into a plurality of second band limited signals. The processing unit is configured to generate a primary pulse pattern based on a first band selected from the plurality of first band limited signals and to generate a secondary pulse pattern based on a second band selected from the plurality of second band limited signals, the first band and the second band being defined by same or substantially overlapping frequency ranges and the implant is configured to receive the primary pulse pattern and the secondary pulse pattern from the processing unit. The primary pulse pattern is configured to stimulate a cochlea of a user of the cochlear implant system during a first time slot, and the secondary pulse pattern is configured to stimulate the cochlea of the user of the cochlear implant system during a second time slot. The first time slot and the second time slot are sequential time slots.

19 Claims, 7 Drawing Sheets

(52) U.S. Cl.
CPC .......... *H04R 25/407* (2013.01); *H04R 25/552* (2013.01); *H04R 2225/67* (2013.01)

(56) References Cited

U.S. PATENT DOCUMENTS

| | | |
|---|---|---|
| 2012/0093329 A1 | 4/2012 | Francart et al. |
| 2014/0330344 A1 | 11/2014 | Mishra et al. |
| 2015/0018897 A1* | 1/2015 | Laudanski .......... A61N 1/36036 607/57 |
| 2015/0265837 A1 | 9/2015 | Kulkarni |
| 2016/0136425 A1 | 5/2016 | Hamacher et al. |

FOREIGN PATENT DOCUMENTS

| | | |
|---|---|---|
| EP | 3 045 204 A1 | 7/2016 |
| EP | 3 108 929 A1 | 12/2016 |

\* cited by examiner

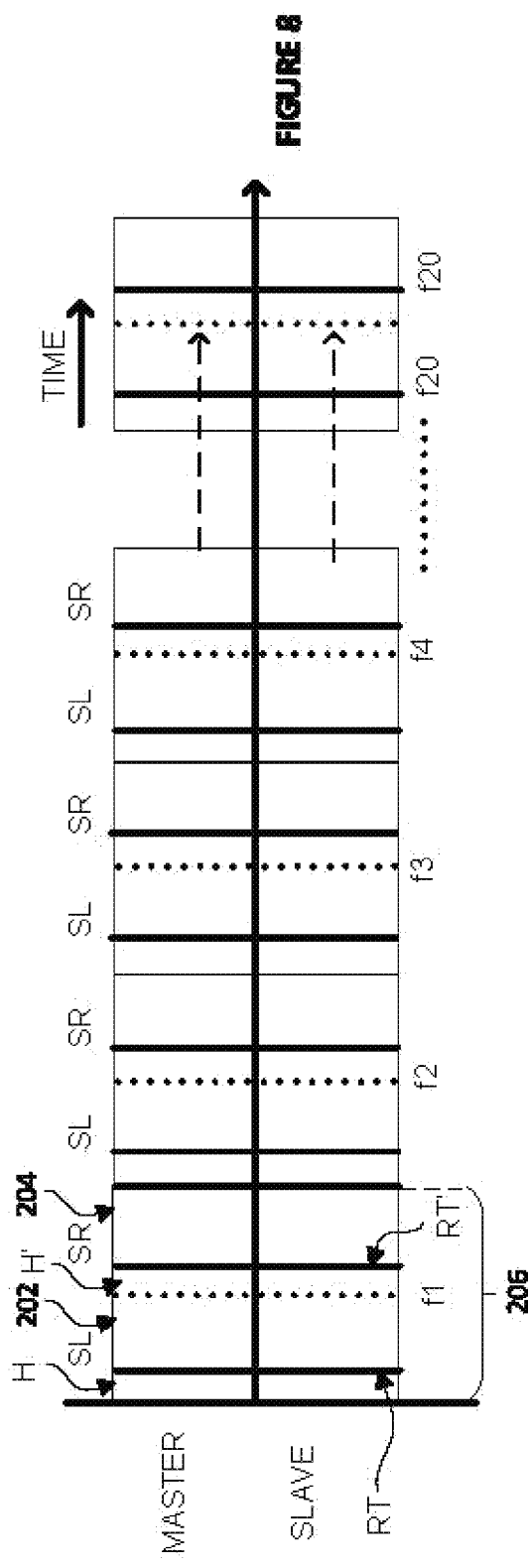
FIGURE 8
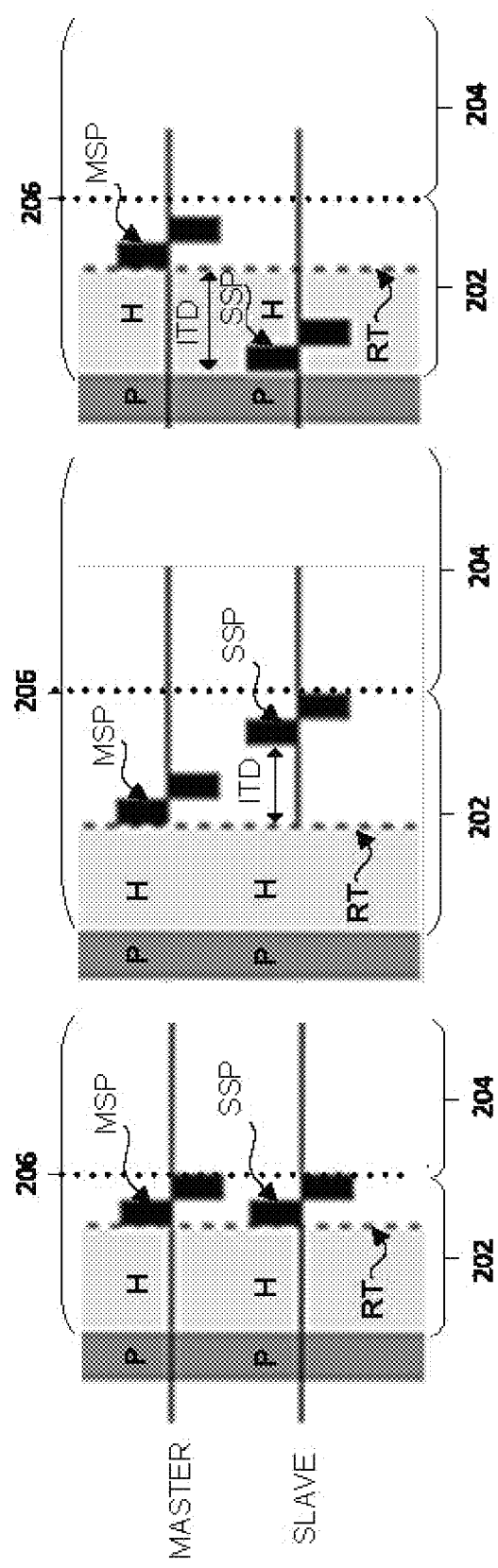
FIGURE 9A
FIGURE 9B
FIGURE 9C

COCHLEAR IMPLANT SYSTEM FOR PROCESSING MULTIPLE SOUND SOURCE INFORMATION

FIELD

The disclosure relates to a cochlear implant system. In particular, the disclosure relates to a cochlear implant system configured to present information to a user of the cochlear implant system when sound is received from multiple sound sources. The disclosure further relates to the cochlear implant system comprising a bilateral cochlear implant system where information comprising different properties (such as spatial cues) from multiple sound sources is presented to the user.

BACKGROUND

A cochlear implant (CI) is a surgically implanted electronic device that provides a perception of sound to a person having a hearing impairment. In some people, cochlear implants may enable sufficient hearing for better understanding of speech. The quality of sound is different from natural hearing, with less sound information being received and processed by the brain. Conventionally, the information received from a single sound source is presented to the user. Until now, no attempt has been made to provide information from multiple sound sources to the CI user. This results in the CI user missing out on an auditory experience that is more natural.

Implanting both cochleas of hearing-impaired listeners with cochlear implants (referred to as bilateral cochlear implants) has become more common in recent years. Using binaural hearing in normal hearing listeners, i.e. where input along the auditory pathway after both ears are presented with the sound are integrated, boosts a person's ability to focus on speech in noisy situations, and allows a person to tune into sounds that are even low in level compared with the competing noise. There is thus a need for an effective system and method for providing these binaural benefits to hearing-impaired subjects, such as those subject that have bilateral cochlear implants.

Improving quality of life for CI users such as by prioritizing improving speech intelligibility in noise, sound localization, and pitch discrimination may require new types of information to be sent to and output by the CI implant.

One such new type of information that would help the CI users are spatial cues, i.e. synchronized information between the two ears. There are two main spatial cues for localizing sound in a plane of azimuth, i.e. angle of a sound source on the horizon relative to a point in the center of the head between the ears, namely (i) interaural time differences (ITDs), and (ii) interaural level differences (ILDs). ILDs are primarily a high-frequency cue, and occur because the listener's head shadowing the sound at the ear contralateral with respect to a sound source. Acoustically ITDs exist at all frequencies, however, normal hearing humans are typically most sensitive to ITDs at 500-900 Hz. In existing cochlear implant systems, the ITDs are not well-coded. It is expected that including such timing information will enhance spatial sound perception.

In an auditory environment (auditory scene) containing multiple sound sources (talkers or other sources of sound), an individual receives a mixed signal from multiple sound sources. Individual with normal hearing is capable of un-mixing the mixed signal and utilize the spatial cues from multiple sound sources along with neural machinery for sound localization and to improve speech intelligibility in the auditory scene.

In a bilateral cochlear implant system comprising microphone(s) for receiving sound from the auditory scene, multiple sounds comprising different properties such as spatial cues are combined at the microphone(s). Unfortunately, users of bilateral cochlear implant system are unable to un-mix the mixed signal received at the microphone(s). Even if the mixed signal is resolved into different unmixed signals, presentation of the un-mixed signals separately to a CIS user is a challenge, thereby limiting information transfer from multiple sound sources.

The disclosure offers a solution that allows for presenting information corresponding to separated distinct sound sources. Such information may include different spatial cues specific to each sound source.

SUMMARY OF THE INVENTION

A cochlear implant (CI) is a surgically-implanted prosthetic device that provides profoundly deaf with sensations of sound. A cochlear implant typically includes an external part that usually sits behind the ear and a second part (implant) that is surgically placed under the skin.

The external part usually includes a) a microphone for picking up the sound signal from the user's environment and generating the incoming microphone signal. The microphone may be placed at the ear or in the vicinity such as behind the ear, in the ear or canal, etc. b) a speech processor selects and processes sounds picked up by the microphone. The speech processor may include the filterbank, processing unit, determination unit, memory etc. and optionally c) a transmitter for transmitting processed microphone signal data such as the data like pulse pattern for generating implant electrode stimulation output. The second part usually includes a) an implantable receiver for receiving the transmitted stimulation data; b) an implanted stimulator such as a pulse generator, which allows the received stimulation data after processing such as charge mapping to be directed towards cochlea. In some embodiments, the data is sent using a series of stimulation pulse. The stimulator may also include a memory, and c) an electrode array comprising a group of electrodes implanted at specific insertion depths in the cochlea such that electrode position within the cochlea replicate or substantially replicate place-frequency mapping along length of cochlear of normal hearing. The electrodes receive the stimulation pulse corresponding to a particular frequency from the stimulator and send impulses via corresponding electrodes and subsequently by way of the auditory nerve to the brain, which recognizes the signals as sound.

The skilled person would appreciate that possible modifications in this generally described CI is possible. For example, a fully implantable CI where all components are implanted in the recipient/user of the cochlear implant is also possible. In this set up, a power source in the fully implantable CI may be inductively charged from outside of the CI recipient. In another example, fully implantable CI may still have the microphones in the external part in order to have better sound capturing capabilities compared to the microphones that are surgically implanted.

The bilateral cochlear implant system includes two implants—one positioned at each ear i.e. a left cochlear implant, and a right cochlear implant. In one embodiment, the left CI and right CI includes separate speech processors. However, in another embodiment, the left CI and the right CI share a common speech processor except for the microphones and their positioning. In both embodiments with separate or common speech processor, microphones relating to each ear are positioned at or in the vicinity of the respective ear, for example, a first microphone receiving sound arriving at the left ear and a second microphone receiving sound arriving at the right ear. The incoming microphone signals from microphones or microphone arrays positioned at each ear are provided to the respective speech processor, which may be a common speech processor. Similarly, the left CI and the right CI may also include separate or common implantable receiver.

According to an embodiment, a cochlear implant system is disclosed. The system includes an input unit, a filterbank, a processing unit and an implant. The input unit is configured to provide a first electrical signal from a first sound source and a second electrical signal from a second sound source. The filterbank is configured to filter the first electrical signal into a plurality of first band limited signals and the second electrical signal into a plurality of second band limited signals. The processing unit is configured to generate a primary pulse pattern based on a first band selected from the plurality of first band limited signals and to generate a secondary pulse pattern based on a second band selected from the plurality of second band limited signals, the first band and the second band being defined by same or substantially overlapping frequency ranges and the implant is configured to receive the primary pulse pattern and the secondary pulse pattern from the processing unit. The primary pulse pattern is configured to stimulate a cochlea of a user of the cochlear implant system during a first time slot, and the secondary pulse pattern is configured to stimulate the cochlea of the user of the cochlear implant system during a second time slot. The first time slot and the second time slot are sequential time slots.

According to an embodiment, the implant is configured to generate the primary stimulation pulse in accordance with the received primary pulse pattern and a secondary stimulation pulse in accordance with the received secondary pulse pattern. The stimulation of the cochlear is based on the primary stimulation pulse during the first time slot and the second stimulation pulse during the second time slot.

The pulse pattern may be understood as bits of information that are transferred from processing unit to the implant, typically using an inductive link. The stimulation pulse may be understood as the charge pulse, define by electric charge amount, generated based on the received bit of information, that is delivered from the implant to the electrode of the implantable electrode array.

In one embodiment, the first time slot and the second time slot are sequentially comprised in a time window. The time window includes a predefined time duration during which an electrode of an electrode array implantable in the cochlea is configured to stimulate an auditory nerve. Each electrode in the electrode array represents a specific frequency channel corresponding to the first band and second band. Such association with a specific frequency channel is usually in accordance with the place-frequency mapping along length of the cochlea.

According to a further embodiment, a plurality of time windows are comprised in a time frame during which one cycle of stimulation at the cochlea is completed. Each time window of the plurality of time windows corresponds to a specific frequency channel assigned to a specific electrode of the electrode array. Each time window comprises sequential time slots during which stimulation corresponding to the first sound source and second sound source for the specific frequency channel is sequentially provided such that the time slots across the time windows are provided in an interleaved manner. The time frame is followed by a subsequent time frame during which a subsequent cycle of stimulation at the cochlea is completed.

Therefore, the above disclosed embodiment describes a stimulation strategy utilizing a time frame comprising a plurality of time windows individually assigned to each electrode. The electrode corresponds to a specific frequency channel and are configured to be activated in response to presence of frequency specific content. Each time window comprises sequential time slots during which stimulation corresponding to the first sound source and second sound source for the specific frequency channel is sequentially provided. Thus, a time frame includes interleaved time slots during which electrodes are activated in response to frequency specific content available from multiple sound sources, such as the first sound source and the second sound source.

Utilizing the above mentioned stimulation strategy allows for providing information from multiple sound sources to the user of the cochlear implant system.

The time frame may be defined as a time period during which all data defining one stimulus pulse is utilized to stimulate the cochlea. One stimulus pulse comprises a plurality of stimulation pulses, representing frequency content of the sound within the time period, across all the electrodes of the electrode array. As generation of the plurality of stimulation pulses is a function of sound content available in the time period, it is understandable that during a particular time frame, only the electrodes corresponding to frequencies having content get activated. Thus, the cycle of stimulation is defined by the stimulus pulse activating electrode corresponding to frequencies having content in assigned time window starting from time window 1 through time window n (for an electrode array having n electrodes). This is repeated again for a subsequent time frame in a subsequent cycle of stimulation. It is apparent that the subsequent time frame includes a plurality of subsequent time windows with each subsequent time window comprising a subsequent interleaved time slots.

It is apparent that during a specific time window, utilization of a time slot to activate an electrode is subject to availability of frequency specific content relating to the frequency channel associated with the electrode. Therefore, in one embodiment, none of the time slots is utilized for activating an electrode, if no data is available from any sound source in the frequency channel associated with the time window containing the time slots, the frequency channel being associated with the electrode. In another embodiment, only a few of the time slots are utilized for activating the electrode, if data available is only from a few sound sources in the frequency channel associated with the time window containing the time slots. In yet another embodiment, all the time slots are utilized for activating the electrode, if data available is from all sound sources such as the first or second sound sources in the frequency channel associated with the time window containing the time slots.

In an embodiment, the input unit includes a microphone configured to receive a mixed electrical signal from the first sound source and the second sound source. Because the sound from the first sound source and the second sound source reaches the microphone, the microphone generates a mixed signal comprising the sound received from the first sound source and the second sound source. The microphone may include a microphone array that is configured to utilize a beamforming algorithm for beamsteering. In general, such beamforming algorithms involve processing the mixed signal from the microphones array in such a way that the array acts as a highly directional microphone. In its simple version, it enhances signals from the front and suppresses signals from other directions. In a more sophisticated version, the enhancement direction can be set to the direction of the target sound "steering beamformer". In other words, beamforming provides a "listening beam" which points to, through e.g. beamsteering, the extracted direction of arrival, and receives, a particular sound source (dominant sound) while attenuating other sounds and noise, including, for example, reflections, reverberations, interference, and sounds or noise coming from other directions or points outside the primary beam. Various direction enhancement beamforming algorithms may be employed in order to improve quality of microphone signal of interest received from the dominant sound source. These algorithms may include, but not limited to, generalized sidelobe canceller (GSC), minimum variance distortionless response (MVDR), robust MVDR, or any other beamforming algorithm. Utilizing such beamforming algorithm based signal extraction techniques allows for creating favorable versions of microphone signal while at the same time attenuate or cancel other unwanted source signals received by the microphone array. Utilizing the direction of arrival information allows the setting of a steering direction and the binaural input allows a very efficient noise reduction with high directivity. For example, steering the beamformer towards target sound such e.g., from behind the user, in front of the user, or at the side of a user, e.g., in a car-cabin situation.

In the disclosure, the beam may be directed towards the dominant sound for example sound received from the first sound source and the microphone array is further configured to receive the sound from the other sound source. In this case, the mix signal represents the sound not only from the target sound source for example from a speaker but also from other sound source such as background music.

In an embodiment, in response to receiving the mixed signal from the microphone, a resolution unit comprised in the cochlear implant system is configured to unmix the mixed electrical signal into the first electrical signal and the second electrical signal. The resolution unit may be configured to include source separation algorithm such that dominant sound and direction of arrival for sounds from multiple sources may be identified. The resolution unit is further configured to utilize the direction of arrival of sounds from the first sound source and the second sound source to unmix the mixed signal into the first electrical signal and the second electrical signal.

In one embodiment, the dominant sound source is identified by slicing the auditory scene surrounding the user into angular subspaces. A target signal detection and/or a voice activity detection on a respective spatial sound signal is performed, the spatial sound signal being generated by a spatial filter that divides sound received from the auditory scene in subspaces. Assuming the target signal to be present in a given subspace, the spatial sound signal of that subspace may have an improved target signal-to-noise signal ratio compared to sound signals which include the total space (i.e. the complete surrounding of a user), or other subspaces (not including the sound source in question). Further, the detection of several sound sources, e.g., talkers in different subspaces may be possible by running voice activity detection in parallel in the different subspaces. There are other techniques that may be implemented in the source separation algorithm, which are described later in the description.

According to another embodiment, which may be combined with the cochlear system described above, a cochlear implant system comprising a bilateral cochlear implant system is disclosed. The system includes a first microphone, a second microphone, a resolution unit, a processing unit and an implant including a pulse generator. The first microphone is configured to be positioned at or in vicinity of a first ear of the user. The first microphone is further configured to generate a first mixed electrical signal in response to receiving a sound from a first sound source and a sound from a second sound source. The second microphone is configured to be positioned at or vicinity of a second ear of the user. The second microphone is further configured to generate a second mixed electrical signal in response to receiving the sound from the first sound source and the sound from the second sound source. The resolution unit is configured to unmix the first mixed electrical signal into a first primary signal and a second primary signal and to unmix the second mixed electrical signal into first secondary signal and a second secondary signal. The first primary signal and the second primary signal correspond to the sound received from the first sound source at the first microphone and the second microphone respectively. The first secondary signal and the second secondary signal correspond to the sound received from the second sound source at the first microphone and the second microphone respectively. The processing unit is configured to generate a first pulse pattern and a second pulse pattern. The first pulse pattern includes i) a first primary pulse pattern corresponding to the first primary signal, and ii) a first secondary pulse pattern corresponding to the first secondary signal. The second pulse pattern comprising i) a secondary primary pulse pattern corresponding to the second primary signal, and ii) a second secondary pulse pattern corresponding to the second secondary signal. The pulse generator is configured to generate a first primary stimulation pulse, a first secondary stimulation pulse, a second primary stimulation pulse and a second secondary stimulation pulse. The first primary stimulation pulse is based on the first primary pulse pattern for stimulating, within the first time slot, a first cochlea corresponding to the first ear. The first secondary stimulation pulse is based on the first secondary pulse pattern for stimulating, within the first time slot, a second cochlea corresponding to the second ear. The second primary stimulation pulse is based on the second primary pulse pattern for stimulating, within the second time slot, the first cochlea corresponding to the first ear. The second secondary stimulation pulse is based on the second secondary pulse pattern for stimulating, within the second time slot, the second cochlea corresponding to the second ear.

According to an embodiment, the first microphone is configured to receive sounds from the first sound source and the second sound source simultaneously; and the second microphone is configured to receive sounds from the first sound source and the second sound source simultaneously. The first microphone and the second microphone may include individual microphone arrays that are individually configured to utilize the beam forming algorithms, thus allowing listening beam to be directed towards a dominant source while still receiving sound from the other sound source resulting in a mixed signal as received from the first sound source and the second sound source at a microphone.

The resolution unit may be configured to estimate direction of arrival from the first sound source and the second sound source in order to unmix the signals. In an embodiment, estimating the direction of arrival relies on combining microphone output signals from the left and right sides of the head to determine the delay between sounds present in the microphone outputs. When sounds emanate from the medial (front or rear) region of the wearer, there is little delay between the microphone output signals. However, this delay increases with increase in the angle of the sound source relative to the medial region. The delay increases from the medial region to either lateral region. This monotonic increase may be translated into direction of arrival of sounds with reference to the midline location between both ears. In another embodiment, the estimation technique relies on the shadowing effect of the human head. The head casts a shadowing effect for sounds located on opposite sides of the head. Due to this head shadowing effect, there may be noticeable level differences (in dB) between microphone output signals. The level difference increases as the sound source moves from the midline location between both ears to side. These two basic mechanisms may be used in direction of arrival algorithm estimation. For example, one such implementation for estimating the direction of arrival of a sound includes the steps of a) forming a reference signal, b) detecting sound with two or more spatially separated, directional or spatially separated directional, microphones to produce two or more output signals, c) calculating the relationships between each of the two or more output signals and the reference signal; and d) estimating the direction of arrival based on differences between the relationships. The reference signal may be formed by detecting sound with a dedicated reference signal microphone, which may be formed by way of a beamformer technique. The differences in the relationships may include the step of calculating interaural time differences, using a time correlation technique. The differences in the relationships may include the step of calculating interaural level differences using power difference measures. The step of calculating the relationships may be carried out across multiple frequency channels.

Numerous techniques are known where left and right microphone signals is compared to derive a direction of arrival estimate. These techniques include; Correlation, Maximum Likelihood (covariance minimisation), Multiple Signal Classification (MUSIC), Estimation of Signal Parameters using Rotational Invariance Techniques (ESPRIT) or Eigen decomposition, and Matrix pencil using an array manifold or triangulation. An example includes a known technique for direction of arrival, which relies on sensory microphone arrays whereby the cross-correlation between the microphone output signals is calculated to determine the delay at which the maximum output power or peak occurs. Thus, the estimates reflect the direction of arrival of dominant sounds.

Many other known techniques are also discussed in cf. e.g. BELL, A. J. et al. *An information maximisation approach to blind separation and blind deconvolution*. Neural Computation, 1995, vol. 7 (6), 1129-1159; Jourjine, A. et al., *Blind separation of disjoint orthogonal signals: Demixing N sources from 2 mixtures*. IEEE International Conference on Acoustics, Speech, and Signal Processing (ICASSP OO), vol. 5, pp. 2985-2988, June 2000; ROWEIS, S. T. *One Microphone Source Separation*. Advances in neural information processing systems, 2001, 793-799; PEDERSEN, M. S. et al. *A survey of convolutive blind source separation methods*. Springer Handbook of Speech Processing. Springer, 2008, 1065-1094; BOLDT, J. B. et al. *Estimation of the ideal binary mask using directional systems*. IWAENC 2008, [Boldt et al., 2008] or combinations hereof, cf. e.g. PEDERSEN, M. S. et al. *Separating Underdetermined Convolutive Speech Mixtures*. ICA 2006, 2006, and [Boldt et al., 2008] PEREZ-LORENZO et al. *Evaluation of generalized cross-correlation method for direction of arrival estimation using two microphone in real environments*. August 2012, 73(8), Applied Acoustics (2012); PAULOSE et al. *Acoustic Source Localization*. Intl. Journal of Advanced Research in Electrical, Electronic and Instrumentation Engg. Vo. 2, Issue 2, February 2013. Additional techniques for source separation is described in European Patent applications EP2192794 and EP 2563045.

In an embodiment, the cochlear implant system includes the filterbank configured to filter the first primary signal into a plurality of first primary band limited signals, the first secondary signal into a plurality of first secondary band limited signals, the second primary electrical signal into a plurality of second primary band limited signals and the second secondary signal into a plurality of second secondary band limited signals. The first pulse pattern and second pulse pattern is generated for corresponding bands, defined by same or substantially overlapping frequency ranges. The corresponding bands are selected from the plurality of first primary band limited signals, plurality of first secondary band limited signals, plurality of second primary band limited signals, and plurality of second secondary band limited signals respectively.

In an embodiment, the first time slot and the second time slot are sequentially comprised in a time window. The time window includes a predefined time duration during which stimulation for a specific frequency channel, defined by the corresponding bands, using a first electrode array implantable in the first cochlea for stimulating the first cochlea and a second electrode array implantable in the second cochlea for stimulating the second cochlea is provided.

According to an embodiment, a plurality of time windows are comprised in a time frame during which one cycle of auditory nerve stimulation at the first cochlea and the second cochlea is completed. Each time window of the plurality of time windows corresponds to a specific frequency channel assigned to a specific binaural electrode pair comprising pairing of an electrode of first electrode array with an electrode of the second electrode array. Each time window comprises sequential time slots during which stimulation corresponding to the first sound source and second sound source for the specific frequency channel is sequentially provided such that the time slots across the time windows are provided in an interleaved manner. Furthermore, the time frame is followed by a subsequent time frame during which a subsequent cycle of the auditory nerve stimulation at the first cochlea and the second cochlea is completed. Thus, a time frame would include interleaved time slots during which electrodes are activated in response to frequency specific content available from multiple sound sources, such as the first sound source and the second sound source.

According to an embodiment, the cochlear implant system further includes a transmitter and an implantable receiver. The transmitter is configured to transmit i) the first pulse pattern and the second pulse pattern from the processing unit to the implant within the time window, or ii) alternatively transmit the first pulse pattern in the first time slot and the second pulse pattern in the second time slot from the processing unit to the implant. The receiver is configured to receive the first pulse pattern and the second pulse pattern within the time window, or ii) alternatively receive the first pulse pattern in the first time slot and the second pulse pattern in the second time slot.

According to an embodiment, the processing unit further includes a determination unit. The determination unit is configured to determine at least one of a primary interaural difference between the first primary signal and second primary signal. The primary interaural difference comprising at least one of primary interaural time difference and primary interaural level difference. The determination unit is further configured to determine a secondary interaural difference between the first secondary signal and second secondary signal. The secondary interaural difference comprising at least one of secondary interaural time difference and secondary interaural level difference.

In different embodiments, the interaural differences are dependent upon the determined direction of arrival of sound. The interaural difference may also include a modified interaural difference, an artificial interaural difference.

In an embodiment, the interaural difference comprises an interaural time difference (ITD) and/or an interaural level difference (ILD). Depending on the direction of arrival, the sound may arrive earlier at one ear of an individual than the other ear. This difference in time between when the sound arrives at one ear versus the other is referred to as the interaural time difference (ITD). The ILD is the difference in level (intensity) between a sound arriving at one ear versus the other, i.e. sound having higher level at ear closer to the sound source.

This may include using the determination unit comprising a level detector, as known in the art, that is configured to determine a first level of the one of the band limited signal from first microphone, a second level of the one of the band limited signal from the second microphone, and a level difference between the first level and second level individually for each sound source.

Additionally or alternatively, the ITD may be calculated as a difference between time-of-arrival of the sound at the first microphone and time-of-arrival of sound at the second microphone individually for each sound source. Alternatively, once the direction of arrival of the sound is extracted, the ITD may be computed by calculating the time of arrival of the sound at one of the microphone and utilizing a head related transfer function to estimate arrival time of the sound at another microphone or microphone array. This may be performed for at least one frequency band of related band limited unmixed microphone signals of the first microphone and second microphone signal. Other conventionally known techniques for estimating ITDs may also be employed.

In another embodiment, the the modified interaural difference includes a modified interaural time difference (mITD) and/or a modified interaural level difference (mILD) for at least one of the sound, represented by one of the unmixed signals, received from a sound source. The modified interaural difference may be obtained by modifying the interaural difference. Such modifications may include at least one of amplifying the interaural difference, frequency shifting the interaural difference, representing the ITD as an ILD or representing the ILD as an ITD. For example, the amplification of the interaural difference may include increasing the delay between the onset time for activating an electrode of an electrode array and onset time for activating an electrode of the another electrode array compared to the determined ITD. Similarly, amplification may include increasing magnitude of the level difference as represented by increased difference in stimulation charges of the stimulation pulses compared to difference in electric charge that is based on the determined ILD. In other modifications such as in frequency transposition, the determined interaural difference, for example the ILD may be transposed to a lower frequency with or without amplification. The other listed modifications would be apparent to the skilled person and no further explanation is provided.

In yet another embodiment, the artificial interaural difference comprises an artificial interaural time difference (aITD) and/or an artificial interaural level difference (aILD) for at least one of the sound, represented by one of the unmixed signals, received from a sound source. Based on the direction of arrival of the sound, the artificial interaural difference may include a predetermined or dynamically selected value that allows for localizing the sound. It is apparent that once the direction of arrival of the sound is extracted, the ear closer to and the ear farther away from the major source is known. Also, it is understandable that the ear closer to the major source may have a higher signal level relative to that of the ear farther away from the major source. Similarly, arrival of the sound at the ear closer to the major source will be earlier than that of the ear farther away from the major source. Hence, in an embodiment, the predetermined selected value may include a value such as X db interaural level difference and/or Y µs interaural time difference between the two ears. These predetermined values may also be frequency band specific and sound source specific.

In an embodiment, the first secondary pulse pattern comprises a copy of the first primary pulse pattern with the primary interaural difference incorporated therein, and the second secondary pulse pattern comprises a copy of the second primary pulse pattern with the secondary interaural difference incorporated therein.

In an embodiment, the first secondary pulse pattern comprises the primary interaural difference information and the secondary pulse pattern comprises the secondary interaural difference information. Furthermore, the pulse generator is configured to i) generate a copy of the first primary pulse pattern, incorporate the primary interaural difference, and generate the first secondary stimulation pulse based on the copy of the first primary pulse pattern incorporating the primary interaural difference, and ii) generate a copy of the second primary pulse pattern, incorporate the secondary interaural difference, and generate the second secondary stimulation pulse based on the copy of the second primary pulse pattern incorporating the secondary interaural difference.

According to the preceding embodiments requiring incorporation of the interaural differences in the copies of the first primary pulse pattern and second primary pulse pattern, incorporation includes increasing or decreasing stimulation level of the copy of the primary pulse patterns relative to stimulation level of the primary pulse patterns according to the determined ILD/modified ILD/artificial ILD for each sound source respectively. Such incorporation may also include a scenario where instead of modifying the level of the copy of the primary pulse patterns in accordance with the determined ILD/modified ILD/artificial ILD, the electric change of the secondary stimulation pulse is set in accordance with the determined ILD/modified ILD/artificial ILD and mapping function without the need to first modifying the level in the copy of primary pulse patterns.

According to the preceding embodiments requiring incorporation of the interaural differences in the copies of the first primary pulse pattern and second primary pulse pattern, incorporation includes associating early-activation or delayed-activation information, based on for example as the determined ITD/modified ITD/artificial ITD information, with the copy of the primary pulse patterns and specific to individual sound sources. For example, such information may be associated with arrival times of the primary pulse patterns and the secondary pulse patterns at the implant within the sound source specific time slots, wherein the difference in arrival times represent the determined ITD/modified ITD/artificial ITD information (described later). Thus, corresponding electrodes of two electrode arrays individually implanted in respective cochlea of the first ear and second ear are activated in accordance with a timing difference, as defined by the timing information that may include determined ITD/modified ITD/artificial ITD.

In yet another embodiment, incorporation of the interaural difference includes a combination of earlier recited two embodiments describing level difference information and timing difference information.

In an embodiment, i) the first secondary pulse pattern comprises a copy of the first primary pulse pattern with the primary interaural level difference incorporated therein, and ii) within the first time slot, the processing unit is configured to align transmission of the first primary pulse pattern and first secondary pulse pattern such that a difference between time of arrival of the first primary pulse pattern and time of arrival of the first secondary pulse pattern at the receiver represents the primary interaural time difference. Additionally or alternatively, the second secondary pulse pattern comprises a copy of the second primary pulse pattern with the secondary interaural level difference incorporated therein; and ii) within the second time slot, the processing unit is configured to align transmission of the second primary pulse pattern and the second secondary pulse pattern such that a difference between time of arrival of the second primary pulse pattern and time of arrival of the second secondary pulse pattern at the receiver represents the secondary interaural time difference.

In one embodiment, a difference between a primary arrival time of the primary pulse pattern and a secondary arrival time of the secondary pulse pattern for each sound within assigned time slot at the receiver determines the activation times of an electrode of the electrode array and a corresponding electrode of the another electrode array respectively, the difference representing the ITD or mITD or aITD.

Thus, the delay in activation of the electrodes of two electrode arrays may be implemented simply by an improved transmission method, where the arrival times of the pulse patterns determines a reference time for activating the primary electrode and a delay relative to the reference time, for example the artificial ITD, in receipt of the secondary pulse pattern or copy of primary secondary pulse pattern. Thus, the data to be transmitted is reduced by expressing desired electrode output timing data as the arrival time of a data message at the implant receiver. Thus, no bits are required to be included in a packet message to provide providing relative activation timing data in the data packet during the transmission. In order to produce proper timing cue, it is apparent that the processing time of the received primary pulse pattern and secondary pulse pattern is accounted for at the second part when utilizing this technique. Usually, the reference time may either follow directly after the processing delay or may be provided after a headroom that is provided after the processing delay. In another implementation, the aITD and/or aILD may be included in a data packet that is transmitted from the processor.

According to an embodiment, an electrode of the first electrode array and an electrode of the second electrode array defined by same of substantially overlapping frequency ranges form a binaural electrode pair. One electrode of the pair is pre-classified or dynamically assigned as a master electrode and another electrode as a slave electrode. The pulse generator may be configured to access the binaural electrode pair information, from a memory, comprising pairing of an electrode of an electrode array with an electrode of the another electrode array, wherein one electrode of the pair is a master electrode and another electrode is a slave electrode. At least one of the first time slot includes a first headroom immediately prior to a first reference time comprised within the first time slot and the second time slot includes a second headroom immediately prior to a second reference time comprised within the second time slot. For each time slot, the pulse generator is configured to specify the interaural time difference relative to the master electrode such that when the interaural time difference is positive, the master electrode is activated at a reference time prior to the slave electrode. For each time slot, the pulse generator is configured to specify the interaural time difference relative to the master electrode such that when the interaural time difference is negative, i) the slave electrode is activated prior to the master electrode such that the master electrode is activated at the first reference time and the slave electrode is activated utilizing the first headroom for stimulation based on the first primary stimulation pulse and first secondary stimulation pulse and ii) the slave electrode is activated prior to the master electrode such that the master electrode is activated at the second reference time and the slave electrode is activated utilizing the second headroom for stimulation based on the second primary stimulation pulse and second secondary stimulation pulse. Alternatively, for each time slot, the pulse generator is configured to specify the interaural time difference relative to the master electrode such that when the interaural time difference is negative, the master electrode is reassigned as a slave electrode and the slave electrode is reassigned as a master electrode, such that the reassigned master electrode is activated at the reference time and prior to the reassigned slave electrode without need of the headroom.

In an embodiment, for each binaural electrode pair during at least one of the first time slot and second time slot, the implant is configured to specify the interaural level difference relative to the master electrode such that when the interaural level difference is positive, the master electrode is activated with a higher electric charge compared to the correspondingly paired slave electrode and when the interaural level difference is negative, the slave electrode of the accessed binaural pair is activated with a higher electric charge compared to the correspondingly paired master electrode.

According to an embodiment, the processing unit is configured to control transmission rate of the pulse patterns from the transmitter to receiver such that the primary pulse pattern and the secondary pulse pattern, or the first pulse pattern and second pulse pattern are transmitted sequentially within the time window comprising the first slot and second slot.

According to an embodiment, the processing unit is configured to determine whether the first band and second band include low frequencies. In another embodiment, the processing unit is configured to determine whether at least one of i) the first primary band limited signal, and first secondary band limited signal, and ii) the second primary band limited signal and a second secondary band limited signal include low frequencies. In both these embodiments, the processing unit is configured to generate stimulation pulse patterns corresponding to at least one of i) both the first band and second band, ii) both the first primary band limited signal, and first secondary band limited signal, and iii) both the second primary band limited signal and a second secondary band limited signal at a generation rate that is lower than a frame rate in response to identification of the band(s)/band limited signal(s) and second band include low frequencies. The frame rate is defined by repetition of the time frames, i.e. frequency of cycle of stimulation. In other words, for low frequency band(s)/band limited signal(s), the processing unit is configured to generate stimulation pulse patterns in time frames that are separated by other time frames where the processing unit is configured to be prevented from generating the stimulation pulse patterns. Thus, the implant is configured to generate and deliver stimulation pulse based on the generated stimulation pulse patterns only in a few time frames, i.e. not in all time frames. Typically, the low frequency include frequencies same or lower than 1000 Hz and the rate of generation of stimulation pulse is usually defined by centre frequency of the band.

According to an embodiment, the processing unit is configured to determine whether the first band and second band include high frequencies. In another embodiment, the processing unit is configured to determine whether at least one of i) the first primary band limited signal, and first secondary band limited signal, and ii) the second primary band limited signal and a second secondary band limited signal include high frequencies. In both these embodiments, the processing unit is configured to generate stimulation pulse patterns corresponding to at least one of i) both the first band and second band, ii) both the first primary band limited signal, and first secondary band limited signal, and iii) both the second primary band limited signal and a second secondary band limited signal at a generation rate that is same as the frame rate in response to identification of the band(s)/band limited signal(s) include high frequencies. The frame rate is defined by repetition of the time frames, i.e. frequency of cycle of stimulation. In other words, for high frequency band(s)/band limited signal(s), the processing unit is configured to generate stimulation pulse patterns in each time frame. Thus, the implant is configured to generate and deliver stimulation pulse based on the generated stimulation pulse patterns in all time frames. Typically, the high frequency include frequencies above than 1000 Hz.

According to an embodiment, the above two preceding embodiments addressing low frequency and high frequency are combinable. The processing unit is configured to determine whether the first band and second band include low frequencies or high frequencies. In another embodiment, the processing unit is configured to determine whether at least one of i) the first primary band limited signal, and first secondary band limited signal, and ii) the second primary band limited signal and a second secondary band limited signal include low frequencies or high frequencies. The processing unit is configured to generate stimulation pulse patterns corresponding to at least one of i) both the first band and second band, ii) both the first primary band limited signal, and first secondary band limited signal, and iii) both the second primary band limited signal and a second secondary band limited signal at a generation rate that is same as the frame rate in response to identification of the band(s)/band limited signal(s) include high frequencies. The processing unit is configured to generate stimulation pulse patterns corresponding to at least one of i) both the first band and second band, ii) both the first primary band limited signal, and first secondary band limited signal, and iii) both the second primary band limited signal and a second secondary band limited signal at a generation rate that is lower than a frame rate in response to identification of the band(s)/band limited signal(s) and second band include low frequencies. Thus, the implant is configured to generate and deliver stimulation pulses based on the generated stimulation pulse patterns in all time frames for high frequencies and only in a few time frames for low frequencies. For example, for low frequency band 100 Hz-200 Hz, the generation rate may be 100 Hz whereas for a high frequency band 2800 Hz-3500 Hz, the generation rate may be 1000 Hz. Thus, the generation rate for generating stimulation pulse patterns for high frequencies is 10 times than the generation rate for generating stimulation pulse patterns of low frequencies. In other words, the stimulation pulse pattern for high frequencies is generated for each of 10 time frames, then the stimulation pulse pattern for low frequencies is generated only in one time frame per 10 time frames.

BRIEF DESCRIPTION OF THE ACCOMPANYING DRAWINGS

The aspects of the disclosure may be best understood from the following detailed description taken in conjunction with the accompanying figures. The figures are schematic and simplified for clarity, and they just show details to improve the understanding of the claims, while other details are left out. The individual features of each aspect may each be combined with any or all features of the other aspects. These and other aspects, features and/or technical effect will be apparent from and elucidated with reference to the illustrations described hereinafter in which:

Figure 6:
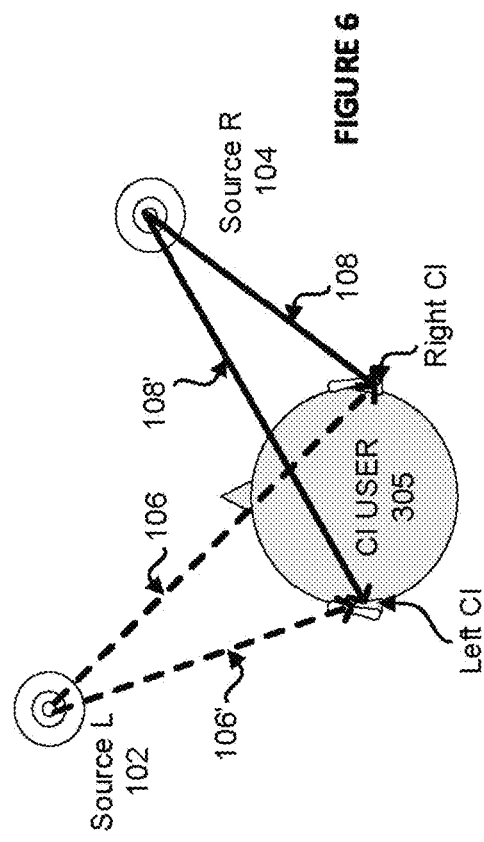
Figure 7:
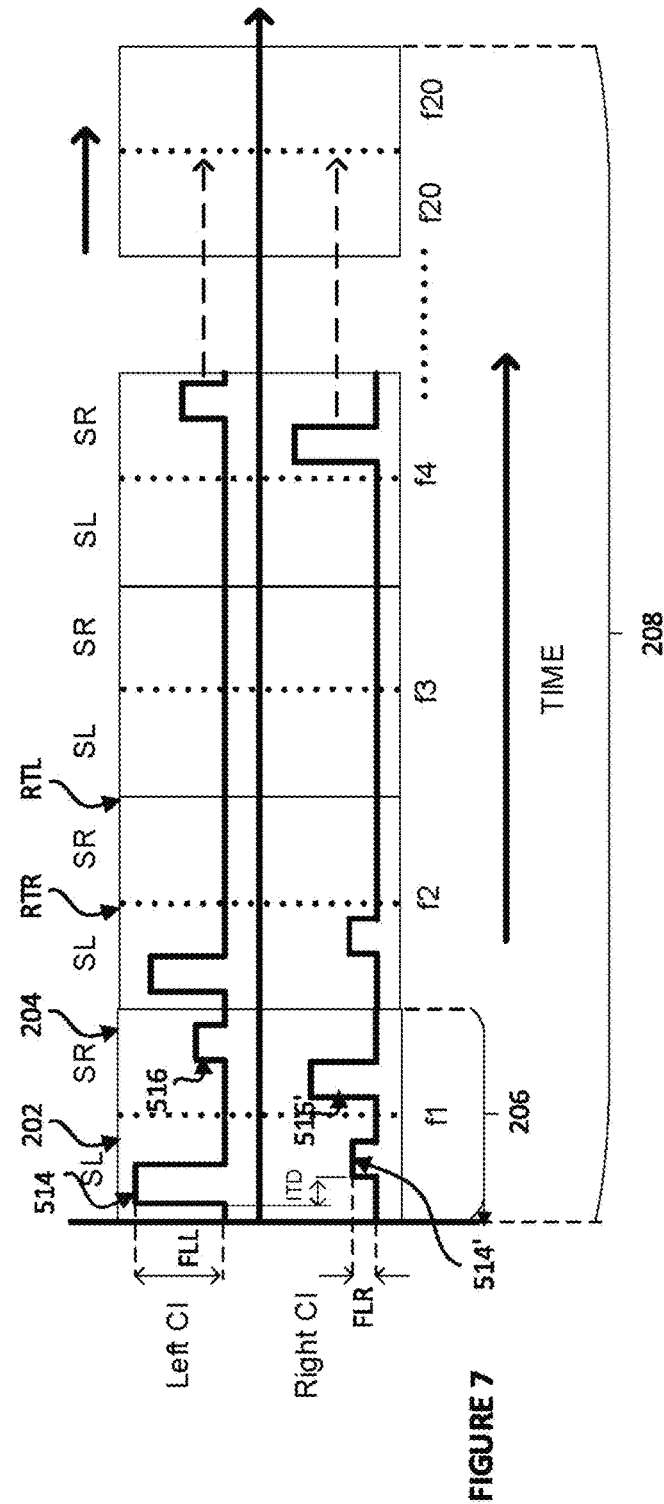
Figure 10:
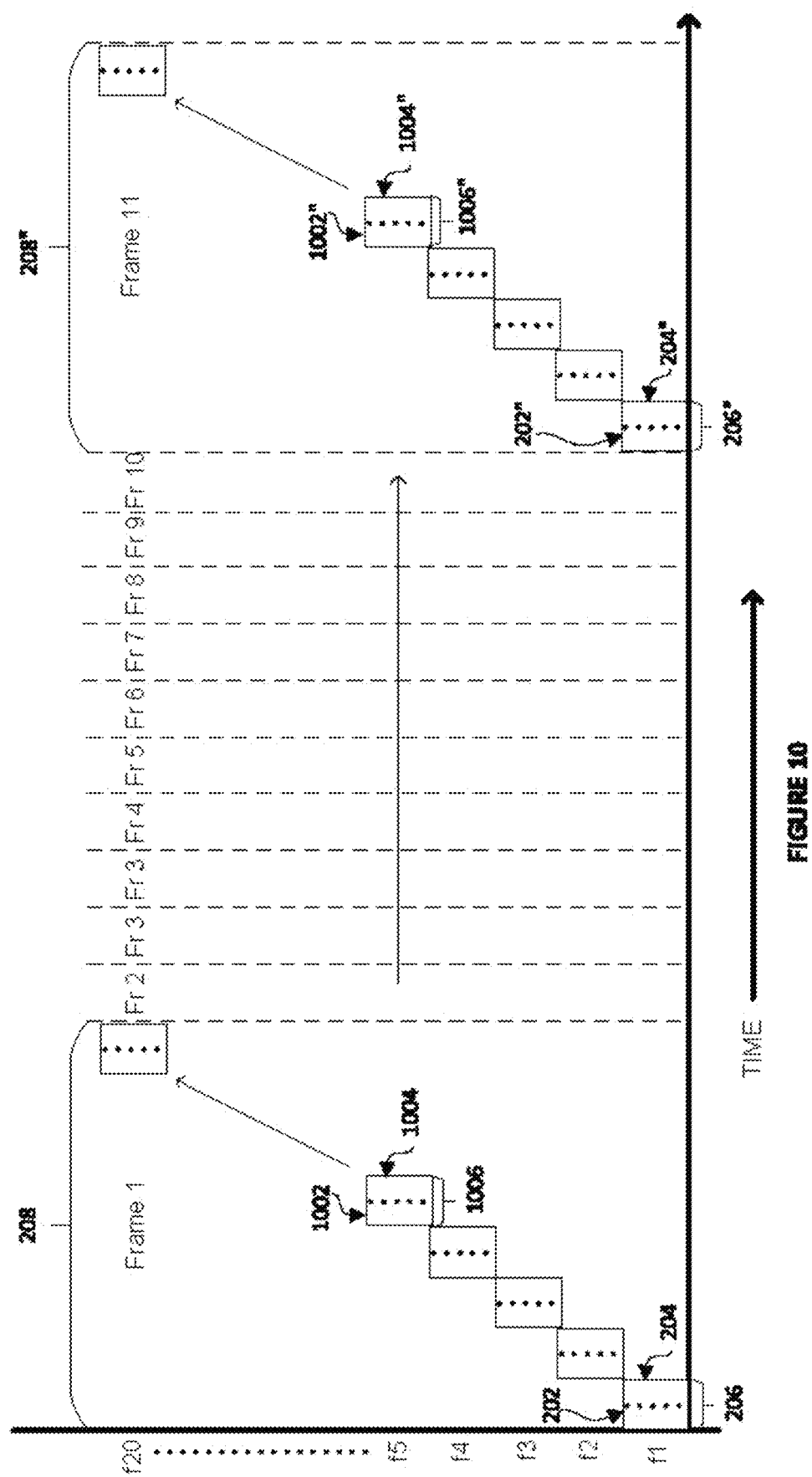

FIG. 6 a CI user using a cochlear implant system configured to receive sound from two sound sources according to an embodiment of the disclosure;

FIG. 7 illustrates sequence for delivering stimulation pulses corresponding to multiple sound sources according to an embodiment of the disclosure;

FIG. 8 illustrates a binaural electrode pair between a master electrode and a slave electrode according to an embodiment of the disclosure;

FIG. 9A illustrates ITD based electrode activation relationship between a master electrode and a slave electrode when ITD=0 according to an embodiment of the disclosure;

FIG. 9B illustrates ITD based electrode activation relationship between a master electrode and a slave electrode when ITD=+ve according to an embodiment of the disclosure;

FIG. 9C illustrates ITD based electrode activation relationship between a master electrode and a slave electrode when ITD=−ve according to an embodiment of the disclosure; and FIG. 10 illustrates stimulation rate in accordance with determined frequency band according to an embodiment of the disclosure.

DETAILED DESCRIPTION

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details.

According to an embodiment, a cochlear implant system 100 is disclosed. The system 100 includes configured to receive a first sound 106 from a first sound source 102, and a second sound 108 from a second sound source 104. The first sound source and the second sound source are usually present in an auditory scene of a user of the cochlear implant system. The microphone is thus configured to provide a mixed electrical signal in response to the sound (106 and 108) received from the first sound source 102 and second sound source 104. The mixed electrical signal comprises a first electrical signal representing the sound received from the first sound source 102 and a second electrical signal representing the sound received from the second sound source.

In one embodiment, as illustrated, a filter bank 114 downstream to the microphone 110 is configured to filter the mixed signal into a plurality of band limited signals 116. The optional beamformer 118 is adapted to produce highly noise reduced signals 120 from the signal 112 and corresponding band limited signal 116. This is made possible by utilizing a microphone that may include a microphone array, which is configured to utilize beamforming algorithm in order to steer the listening beam towards a target source for example towards source 102 in order to improve signal to noise ratio, while still receiving sound from other sound source like source 104. A resolution unit 122 is configured to unmix the plurality of band limited signals into a plurality of first band limited signals and a plurality of second band limited signals, wherein the plurality of first band limited signals correspond to the first electrical signal and the plurality of second band limited signals correspond to the second electrical signal.

In another embodiment, the resolution unit 122 is downstream to the microphone but upstream to the filter bank 114. Thus, the resolution unit 122 is then configured to unmix the unmix the mixed electrical signal received from the microphone 110 into the first electrical signal and the second electrical signal. The filterbank 114 is configured to receive the first electrical signal and the second electrical signal and to filter the first electrical signal into a plurality of first band limited signals and the second electrical signal into a plurality of second band limited signals. The optional beamformer 118 is adapted to produce highly noise reduced signals 120 from the signal 112 and corresponding band limited signal. This is made possible by utilizing a microphone that may include a microphone array, which is configured to utilize beamforming algorithm in order to steer the listening beam towards a target source for example towards source 102 in order to improve signal to noise ratio, while still receiving sound from other sound source like source 104. The processing unit 128 is configured to receive the plurality of first band limited signals 126 and the plurality of second band limited signals 128. In one embodiment, these band limited signals may be received either from the resolution unit 122 directly (as illustrate). In alternative embodiment, the band limited signals are received from filterbank 114/beamformer 118 if the resolution unit 122 is downstream to the microphone 110 but upstream to the filterbank 114.

The processing unit 128 is configured to generate a primary pulse pattern 130 based on a first band selected from the plurality of first band limited signals 124 and to generate a secondary pulse pattern 132 based on a second band selected from the plurality of second band limited signals 126. The first band and the second band are defined by same or substantially overlapping frequency ranges. The system may further include a transmitter 134 configured to transmit the generated pulse patterns (130, 132) as a coded data stream 136, typically over an inductive link. An implant 150 comprising a receiver 138 is configured to receive the primary pulse pattern and the secondary pulse pattern from the processing unit. The primary pulse pattern 130 is configured to stimulate a cochlea of a user of the cochlear implant system 100 during a first time slot (202, see FIG. 4), and the secondary pulse pattern 132 is configured to stimulate the cochlea of the user of the cochlear implant system 100 during a second time slot (204, see FIG. 4). The first time slot and the second time slot are sequential time slots, as illustrated as 202 and 204 in FIG. 4. This may be achieved by a pulse generator 140 comprised in the implant 150. The pulse generated is configured to receive the primary pulse pattern 130 and secondary pulse pattern 132 and to generate a primary stimulation pulse and a secondary stimulation pulse. The pulse generator 140 is configured to deliver the primary stimulation pulse 142, during the first time slot (202, see FIG. 4) to an electrode 148 of an electrode array 146. The electrode 148 corresponds to the frequency channel representing the frequency range of first band and the second band. The pulse generator 140 is further configured to deliver the secondary stimulation pulse 144, during the second time slot (204, see FIG. 4) to the electrode 148 of the electrode array 146. The electrode 148 corresponds to the frequency channel representing the frequency range of first band and the second band. The disclosed cochlear system is configured to allow for providing information from multiple sound sources to the user of a cochlear implant system, thus allowing for improving listening experience of the user.

The pulse pattern may be understood as bits of information that is transferred from processing unit to the implant, typically using an inductive link. The stimulation pulse may be understood as the charge pulse, generated based on the received bits of information, that is delivered from the implant to the electrode of the implantable electrode array.

Figure 1:
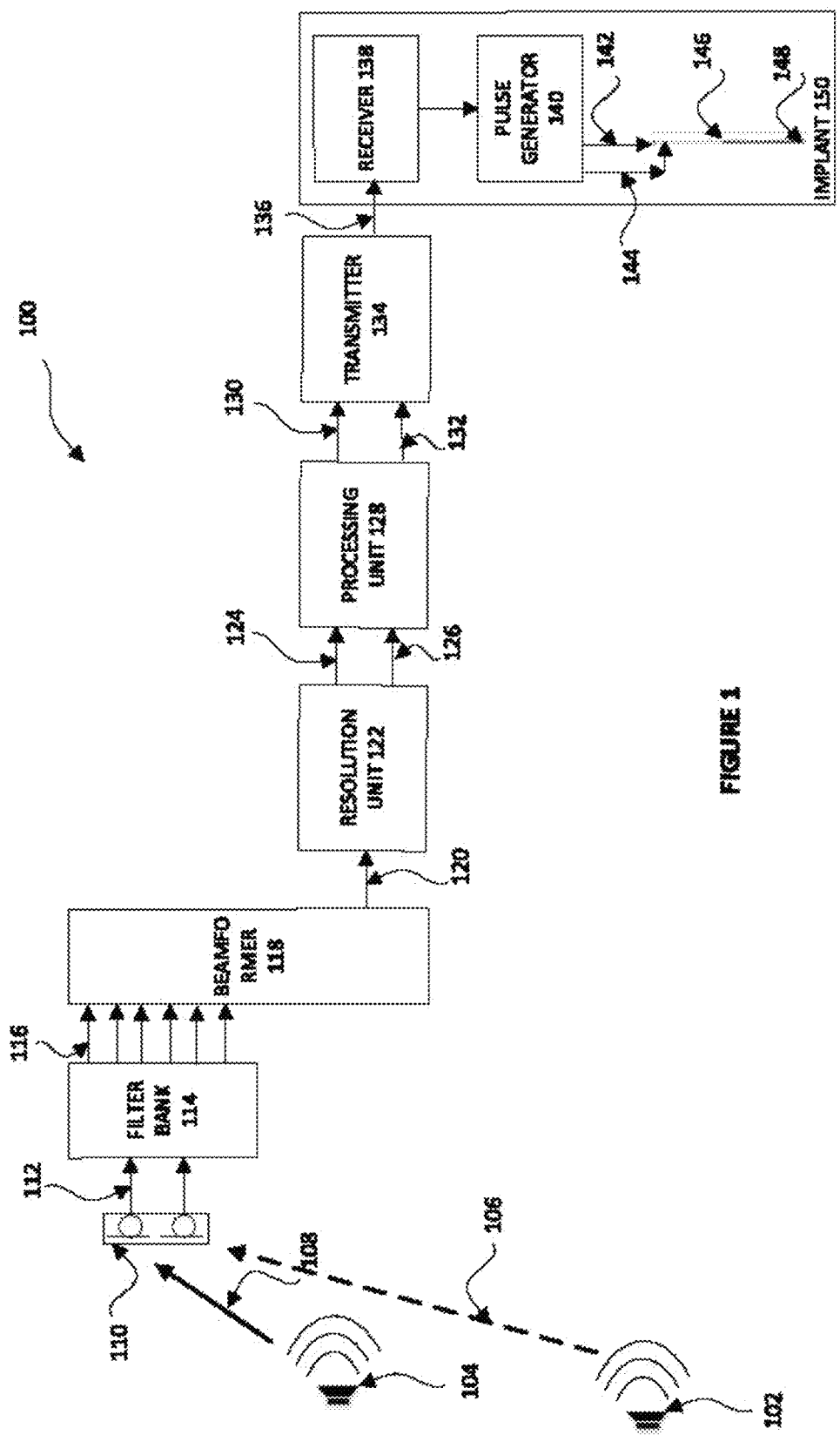
FIG. 1 illustrates a cochlear implant system according to an embodiment of the disclosure.
Figure 2:
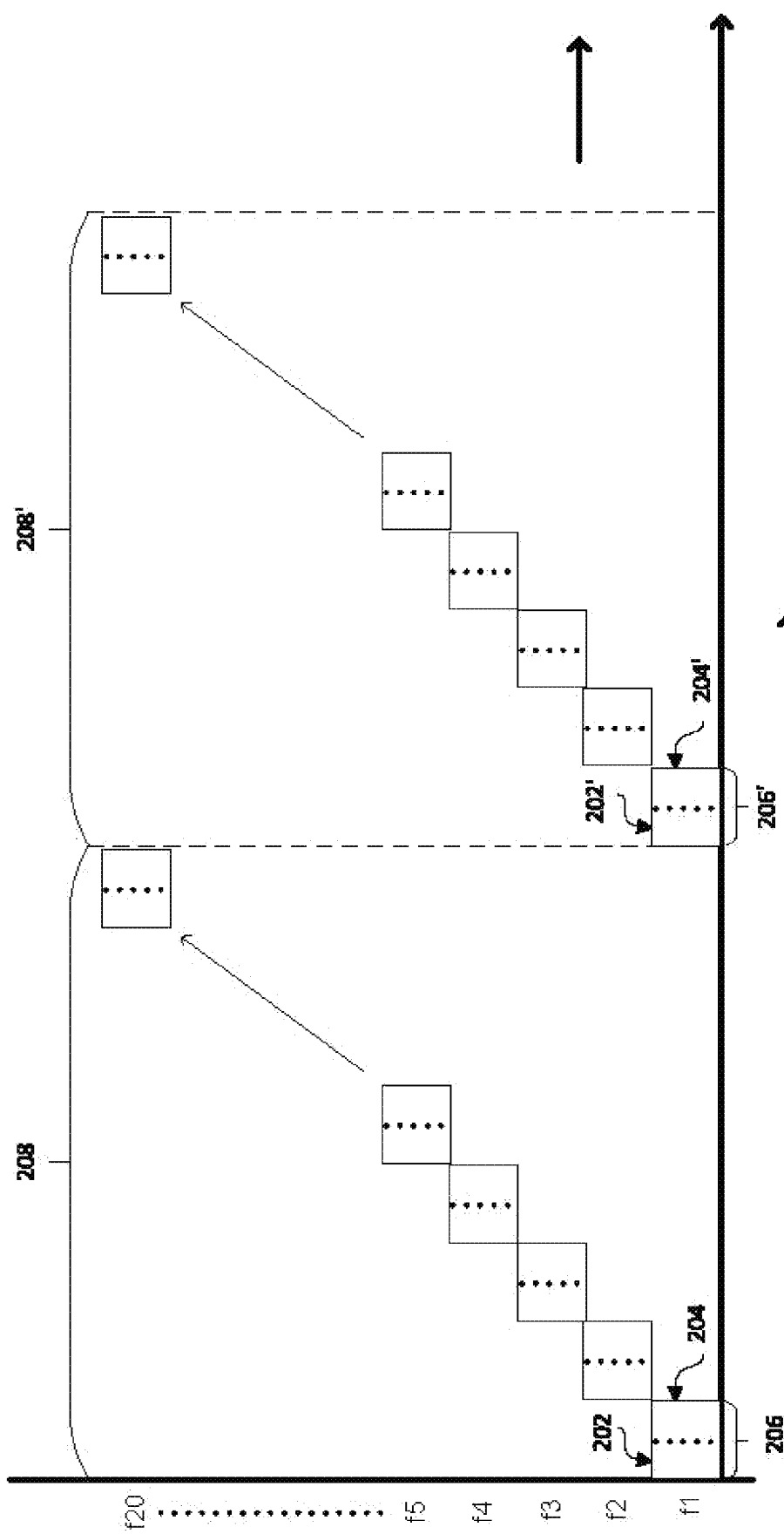
FIG. 2 illustrates interleaved time slots across a plurality of time windows according to an embodiment of the disclosure.

FIG. 2 illustrates interleaved time slots across a plurality of time windows according to an embodiment of the disclosure. As shown, the first time slot 202 and the second time slot 204 are sequentially comprised in a time window 206. The time window includes a predefined time duration (for example, as defined by width of 206) during which an electrode (such as 148, FIG. 1) of an electrode array implantable in the cochlea is configured to stimulate an auditory nerve. The electrode is associated with a specific frequency channel corresponding to the first band and second band. For example, the electrode 148 may be associated with a low frequency channel f1. Similarly, for other frequency channels f2, f3, and so on, sequential time slots for each sound source such as the first sound source and the second sound source are defined. The pulse generator is configured to provide a sound source specific stimulation for a particular frequency channel within a specific time slot assigned to the sound source. In this and other figures, the illustration is provided with a non-limiting example of an electrode array comprising 20 electrodes, as represented by frequency channels f1, f2 . . . f20.

According to an embodiment, a plurality of time windows are comprised in a time frame 208 during which one cycle of stimulation at the cochlea is completed. Each time window such as 206 of the plurality of time windows corresponds to a specific frequency channel such as f1 assigned to a specific electrode (148, FIG. 1) of the electrode array (146, FIG. 1). Each time window such as 206 comprises sequential time slots (202, 204) during which stimulation corresponding to the first sound source (102, FIG. 1) and second sound source (104, FIG. 2) for the specific frequency channel (such as f1) is sequentially provided such that the time slots across the time windows are provided in an interleaved manner. The time frame 208 is followed by a subsequent time frame 208'during which a subsequent cycle of stimulation at the cochlea is completed. The subsequent time frame 208'includes a plurality of frequency channel specific time windows such as 206', with each time window comprising sequential time slots such as 202' and 204' in order to provide stimulation corresponding to band limited signal corresponding to the first sound source (102, FIG. 1) and second sound source (104, FIG. 1).

Figure 3:
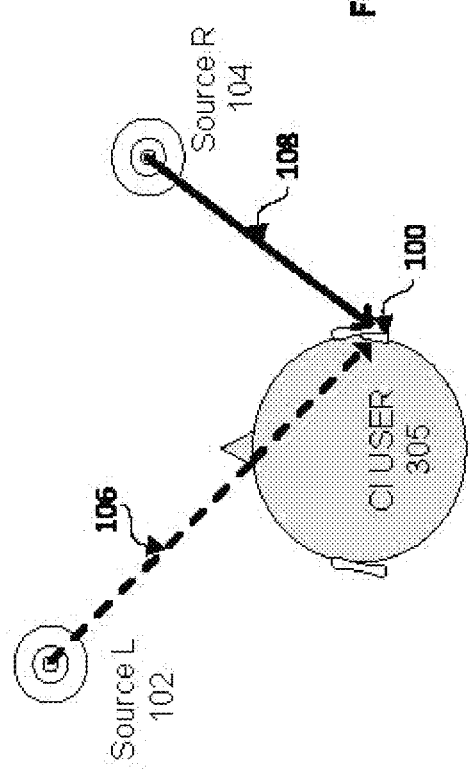
FIG. 3 illustrates a CI user using a cochlear implant system configured to receive sound from two sound sources according to an embodiment of the disclosure.

FIG. 3 illustrates a CI user using a cochlear implant system configured to receive sound from two sound sources according to an embodiment of the disclosure. A user 305 having a cochlear implant system 100 positioned on one side is illustrated. Two sound sources 102 and 104 are present in the auditory scene of the user 305. The microphone comprised in the cochlear implant system 100 is configured to receive sounds 106 and 108 from the first sound source 102 and second sound source 104 respectively. The sound sources 102 and 104 are located at a different location with respect to the user. In the illustration, it is apparent that the sound from the first sound source 102 would reach the cochlear implant system 100 later than the sound received from the second sound source 104. The magnitude of sound reaching from the first sound source 102 and the second sound source 104 is dependent upon individual level and are not inter-related. Because the sound is received from the first sound source 102 and second sound source 104 at the microphone of the cochlear implant system 100, the microphone is configured to generate a mixed signal. However, as explained earlier, the resolution unit (122, FIG. 1) of the cochlear implant system 100 is configured to unmix the mixed signal into a first electrical signal and second electrical signal. The first electrical signal and the second electrical signal may be filtered into a plurality of first band limited signals and second band limited signals respectively. These bands are typically defined by same of substantially overlapping frequency ranges.

Figure 4:
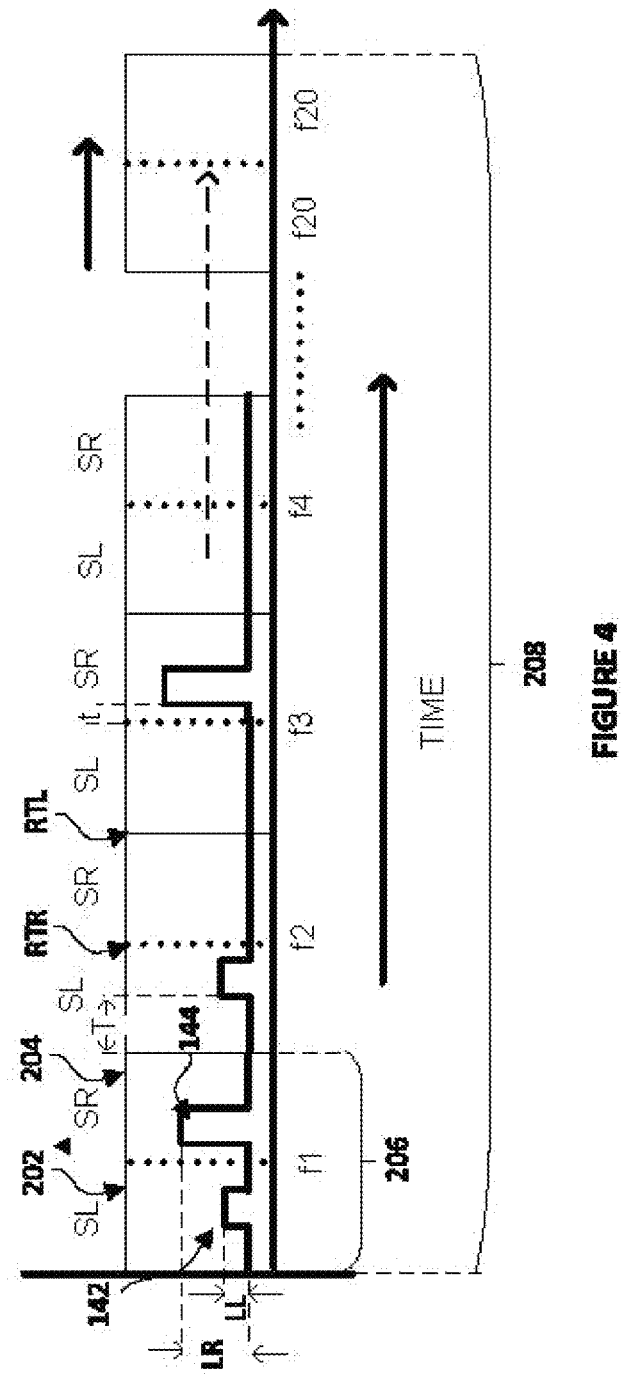
FIG. 4 illustrates sequence for delivering stimulation pulses corresponding to multiple sound sources according to an embodiment of the disclosure.

FIG. 4 illustrates sequence for delivering stimulation pulses corresponding to multiple sound sources according to an embodiment of the disclosure. The pulse generator (140, FIG. 1) is configured to generate the primary stimulation pulse (142, FIG. 1) and secondary stimulation pulse (144, FIG. 1). The pulse generator is further configured to deliver the primary stimulation pulse 142 and the secondary stimulation pulse 144, corresponding to a band, to an electrode associated with a frequency channel representing the band in a first time slot and second time slot respectively. The stimulation pulse are characterized by electric charge corresponding levels of the received sound. The conversion of level into electric charge for a specific frequency channel is a function of a mapping function, which also takes into account threshold (T) and uncomfortable (C) levels of the user. Such mapping is disclosed in EP patent application EP3045204 (for example in FIGS. 2-4), which is incorporated herein by reference. In the illustration, for a frequency channel f1, data is available from both the first sound source and the second sound source. Therefore, the pulse generator is configured to deliver the first stimulation pulse of charge amount, corresponding to level LL of the signal received from the first sound source, in the first time slot 202. The pulse generator is configured to deliver the second stimulation pulse of charge amount, corresponding to level LR of the signal received from the second sound source, in the second time slot 204. However, generation and delivery of the stimulation pulse is a function of whether sound from a particular sound source is available in a certain frequency channel. For example, for frequency channel f2, there is audio content in the sound received from the first sound source and not from the second sound source. Therefore, the stimulation pulse is represented only for the first sound source. Similarly, if the audio content is only available for the second sound source for a specific frequency channel, the stimulation pulse is generated and delivered only for that sound source, as illustrate for frequency channel f3.

RTL and RTR represents the reference times for each time slot, i.e. the starting point of the first time slot and the second time slot or reference point based on which timing information is provided. The pulse generator may be configured to provide sound source proximity information to the cochlear implant system by utilizing relative timing information for each sound source in relation to respective reference time. The pulse generator is configured to utilize time gap between respective reference time and delivery of respective stimulation pulse in the assigned time slot to represent the proximity. For example, sound source 104 is closer to the CI system than the sound source 102. Therefore, time t from respective reference point RTR for the second source 102 is shorter than T, which represents time T from respective reference point RTL. SL and SR represents the time slots assigned to the first sound source 102 and second sound source 104 respectively.

Figure 5:
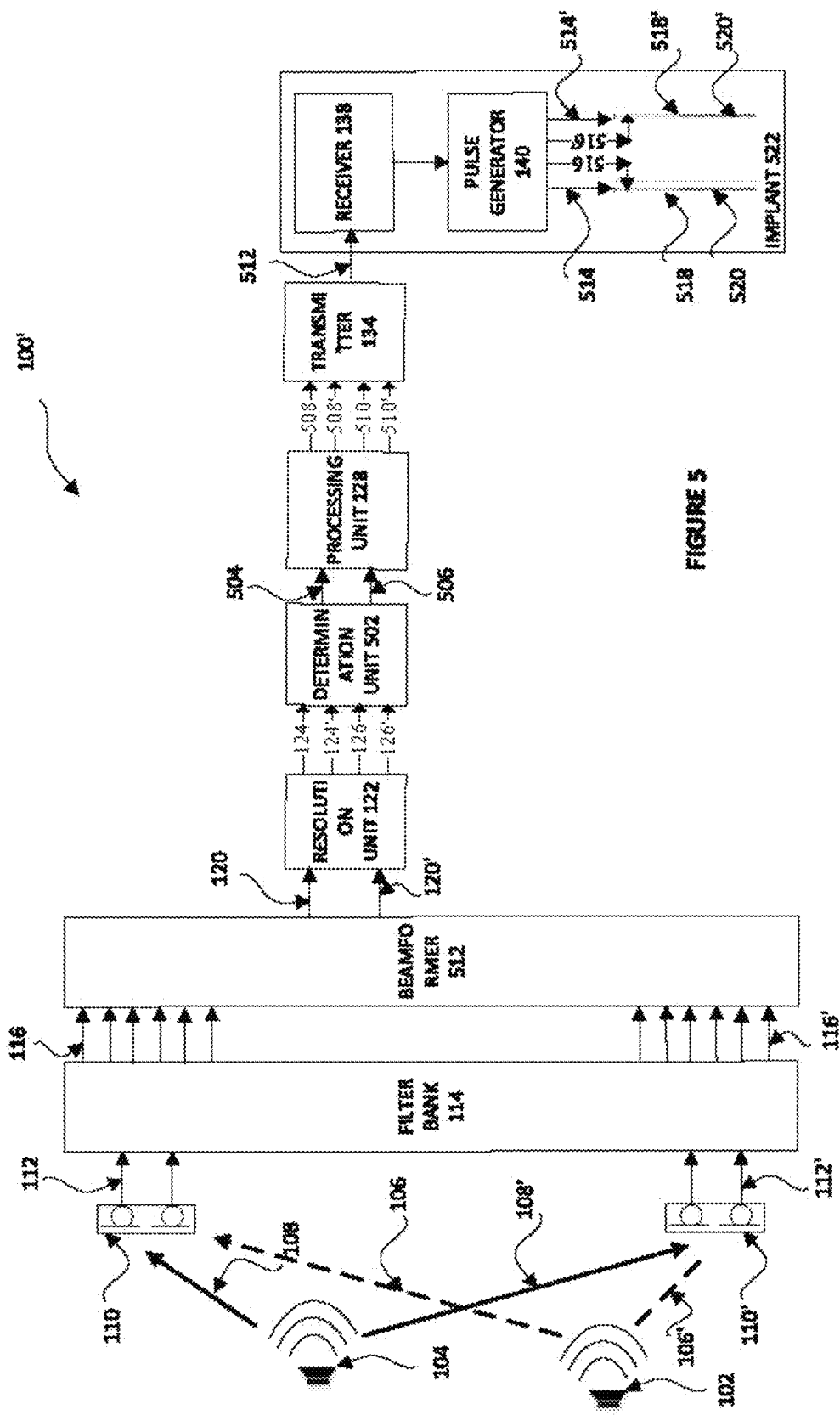
FIG. 5 illustrates a cochlear implant system comprising a bilateral cochlear implant system according to an embodiment of the disclosure.

FIG. 5 illustrates a cochlear implant system comprising a bilateral cochlear implant system according to an embodiment of the disclosure. The bilateral cochlear implant system 100' includes a first microphone 110 configured to be positioned at or in vicinity of a first ear of the user and a second microphone 110' configured to be positioned at or vicinity of a second ear of the user. The first microphone is configured to receive sound (106, 108) from a first sound source 102 and a second sound source 104. The first microphone is configured to generate a first mixed electrical signal 112 in response to receiving the sound 106 from the first sound source 102 and the sound 108 from a second sound source 104. The second microphone is configured to receive sound (106', 108') from the first sound source 102 and second sound source 104. The second microphone 110' is configured to generate a second mixed electrical signal 112' in response to receiving the sound 106' from the first sound source 102 and the sound 108' from the second sound source 104.

A resolution unit 122 is configured to unmix the first mixed electrical signal 112 into a first primary signal 124 and a second primary signal 124' and to unmix the second mixed electrical signal 112' into a first secondary signal 126 and a second secondary signal 126'. The first primary signal 124 and the second primary signal 124' correspond to the sound (106, 106') received from the first sound source 102 at the first microphone 110 and the second microphone 110' respectively. The first secondary signal 126 and the second secondary signal 126' corresponding to the sound (108, 108') received from the second sound source 106 at the first microphone 110 and the second microphone 110' respectively.

In one embodiment, the resolution unit 122 is downstream to the microphones 110, 110' but upstream to a filterbank 114 in signal processing chain. The filterbank 114 downstream to the resolution unit 122 is configured to filter the first primary signal 124 into a plurality of first primary band limited signals, the first secondary signal 126 into a plurality of first secondary band limited signals, the second primary signal 124' into a plurality of second primary band limited signals and the second secondary signal 126' into a plurality of second secondary band limited signals. The optional beamformer 512 is adapted to produce highly noise reduced signals. This is made possible by utilizing a microphones that may individually include a microphone arrays, which is configured to utilize beamforming algorithm in order to steer the listening beam towards a target source for example towards source 102 in order to improve signal to noise ratio, while still receiving sound from other sound source like source 104.

In another embodiment, the first mixed electrical signal 112 and second mixed electrical signal 112' are first filtered using the filterbank 114 to generate a plurality of first band limited mixed signals 116 based on the first mixed electrical signal 112 and to generate a plurality of second band limited mixed signals 116' based on the second mixed electrical signal 112'. The optional beamformer 512 is adapted to produce highly noise reduced signals. This is made possible by utilizing a microphones that may individually include a microphone arrays, which is configured to utilize beamforming algorithm in order to steer the listening beam towards a target source for example towards source 102 in order to improve signal to noise ratio, while still receiving sound from other sound source like source 104. Thereafter, plurality of bands having better signal-to-noise ratio 120, 120' are unmixed using the resolution unit 122. Thus, the resolution unit is configured to unmix the plurality of mixed signals into a plurality of first primary band limited signals, a plurality of first secondary band limited signals, a plurality of second primary band limited signals and a plurality of second secondary band limited signals.

The processing unit 128 is configured to generate a first pulse pattern comprising i) a first primary pulse pattern 508 corresponding to the first primary signal 124, and ii) a first secondary pulse pattern 508' corresponding to the first secondary signal 124'. The processing unit is further configured to generate a second pulse pattern comprising i) a secondary primary pulse pattern 510 corresponding to the second primary signal 124', and ii) a second secondary pulse pattern 510' corresponding to the second secondary signal 126'. The implant 522 includes a pulse generator 140 configured to generate i) a first primary stimulation pulse 514 based on the first primary pulse pattern 508 for stimulating, within the first time slot (202, FIG. 7), a first cochlea corresponding to the first ear, and ii) a first secondary stimulation pulse 514' based on the first secondary pulse pattern 510' for stimulating, within the first time slot (202, FIG. 7), a second cochlea corresponding to the second ear. The pulse generator 140 is further configured to generate i) a second primary stimulation pulse 516 based on the second primary pulse pattern 510 for stimulating, within the second time slot (204, FIG. 7), the first cochlea corresponding to the first ear, and ii) a second secondary stimulation pulse 516' based on the second secondary pulse pattern 510' for stimulating, within the second time slot (204, FIG. 7), the second cochlea corresponding to the second ear. An electrode array 518 comprising electrodes such as 520 is implantable in the first ear and an electrode array 518' comprising electrodes such as 520' is implantable in the second ear.

In one embodiment, as illustrated, a filter bank 114 downstream to the microphone 110 is configured to filter the mixed signal into a plurality of band limited signals 116. The optional beamformer 118 is adapted to produce highly noise reduced signals 120 from the signal 112 and corresponding band limited signal 116. This is made possible by utilizing a microphone that may include a microphone array, which is configured to utilize beamforming algorithm in order to steer the listening beam towards a target source for example towards source 102 in order to improve signal to noise ratio, while still receiving sound from other sound source like source 104. A resolution unit 122 is configured to unmix the plurality of band limited signals into a plurality of first band limited signals and a plurality of second band limited signals, wherein the plurality of first band limited signals correspond to the first electrical signal and the plurality of second band limited signals correspond to the second electrical signal.

In another embodiment, the resolution unit 122 is downstream to the microphone but upstream to the filter bank 114. Thus, the resolution unit 122 is then configured to unmix the unmix the mixed electrical signal received from the microphone 110 into the first electrical signal and the second electrical signal. The filterbank 114 is configured to receive the first electrical signal and the second electrical signal and to filter the first electrical signal into a plurality of first band limited signals and the second electrical signal into a plurality of second band limited signals. The optional beamformer 118 is adapted to produce highly noise reduced signals 120 from the signal 112 and corresponding band limited signal. This is made possible by utilizing a microphone that may include a microphone array, which is configured to utilize beamforming algorithm in order to steer the listening beam towards a target source for example towards source 102 in order to improve signal to noise ratio, while still receiving sound from other sound source like source 104.

The system may further include a determination unit 502 configured to determine at least one of a primary interaural difference between the first primary signal 124 and second primary signal 126. The primary interaural difference comprising at least one of primary interaural time difference and primary interaural level difference. The determination unit is further configured to determine a secondary interaural difference between the first secondary signal 124' and second secondary signal 126'. The secondary interaural difference comprising at least one of secondary interaural time difference and secondary interaural level difference. The processing unit may be configured to generate the first pulse pattern and second pulse pattern in accordance with the primary interaural difference and/or secondary interaural difference respectively.

In an embodiment, the first pulse pattern and second pulse pattern is generated for corresponding bands, defined by same or substantially overlapping frequency ranges, selected from the plurality of first primary band limited signals, plurality of first secondary band limited signals, plurality of second primary band limited signals, and plurality of second secondary band limited signals respectively.

In an embodiment, the system further includes a transmitter 134 configured to transmit i) the first pulse pattern and the second pulse pattern from the processing unit 128 to the implant 522 within the time window ((206, FIG. 7), or ii) alternatively transmit the first pulse pattern in the first time slot ((202, FIG. 7) and the second pulse pattern in the second time slot (204, FIG. 7) from the processing unit 128 to the implant 522. Such transmission is generally in form of the pulse patterns being transmitted, generally inductively, as encoded data 512. The receiver 138 configured to receive the first pulse pattern and the second pulse pattern within the time window (206, FIG. 7), or ii) alternatively receive the first pulse pattern in the first time slot (202, FIG. 7) and the second pulse pattern in the second time slot (204, FIG. 7).

FIG. 6 illustrates a CI user using a cochlear implant system configured to receive sound from two sound sources according to an embodiment of the disclosure. A user 305 having a bilateral cochlear implant system as the left ear (left CI) and right ear (Right CI) is shown. Two sound sources (first sound source 102 and second sound source 104) are present in the auditory scene of the user 305. A first microphone (110, Right CI) comprised in the Right CI is configured to receive sounds 106 and 108 from the first sound source 102 and second sound source 104 respectively. The first microphone is configured to generate a first mixed electrical signal (112, FIG. 6). A second microphone (110', Left CI) comprised in the Left CI is configured to receive sounds 106' and 108' from the first sound source 102 and second sound source 104 respectively. The second microphone is configured to generate a second mixed electrical signal (112', FIG. 6). The sound sources 102 and 104 are located at a different location with respect to the user. In the illustration, it is apparent that the sound 106' from the first sound source 102 would reach the Left CI prior to the sound 106 reaching the Right CI. Similarly, the sound 108 from the second sound source 104 would reach the Right CI prior to the soured 108' reaching the Left CI. The magnitude of sound reaching from the first sound source 102 and the second sound source 104 at a specific CI (Right or Left) is dependent upon individual level at the Left CI and Right CI. However, the sound reaching the Left CI and Right CI are generally inter-related, for example based on attenuation Head Related Transfer Function (HRTF). As explained earlier, the resolution unit (122, FIG. 5) of the cochlear implant system 100 is configured to unmix the first electrical mixed signal into a first primary signal and second primary signal and to unmix the second electrical mixed signal into first secondary signal and a second secondary signal.

FIG. 7 illustrates sequence for delivering stimulation pulses corresponding to multiple sound sources according to an embodiment of the disclosure. The first time slot 202 and the second time slot 204 are sequentially comprised in a time window 206. The time window 206 includes a predefined time duration (for example width of 206) during which stimulation for a specific frequency channel such as f1 (relating to electrodes 520 and 520', FIG. 5), defined by the corresponding bands, using a first electrode array (520, FIG. 5) implantable in the first cochlea for stimulating the first cochlea and a second electrode array (520', FIG. 5) implantable in the second cochlea for stimulating the second cochlea is provided. A plurality of time windows are comprised in a time frame (208) during which one cycle of auditory nerve stimulation at the first cochlea and the second cochlea is completed. Each time window such as 206 of the plurality of time windows corresponds to a specific frequency channel such as f1 assigned to a specific binaural electrode pair comprising pairing of an electrode (520, FIG. 5) of first electrode array (518, FIG. 5) with an electrode (520', FIG. 5) of the second electrode array (518', FIG. 5). Each time window such as 206 includes sequential time slots (202, 204) during which stimulation corresponding to the first sound source (102, FIG. 6) and second sound source (104, FIG. 6) for the specific frequency channel is sequentially provided such that the time slots across the time windows are provided in an interleaved manner. The time frame 208 is followed by a subsequent time frame (208', FIG. 2) during which a subsequent cycle of the auditory nerve stimulation at the first cochlea and the second cochlea is completed.

The pulse generator (140, FIG. 5) is configured to generate the first primary stimulation pulse (514, FIG. 5), first secondary stimulation pulse (514', FIG. 5), second primary stimulation pulse (516, FIG. 5) and second secondary stimulation pulse (516', FIG. 5). The pulse generator is configured to deliver the first primary stimulation pulse and first secondary stimulation pulse, corresponding to a band, to an electrode (520, FIG. 5) associated with a frequency channel f1 representing the band in a first time slot 202. The pulse generator is configured to deliver the second primary stimulation pulse and second secondary stimulation pulse, corresponding to a band, to an electrode (520, FIG. 5) associated with a frequency channel f1 representing the band in a second time slot 204.

The stimulation pulses are characterized by electric charge corresponding levels of the received sound. The conversion of level into electric charge for a specific frequency channel is a function of a mapping function, which also takes into account threshold (T) and uncomfortable (C) levels of the user. Such mapping is disclosed in EP patent application EP3045204 (for example in FIGS. 2-4), which is incorporated herein by reference. The generation and delivery of the stimulation pulse is a function of whether sound from a particular sound source is available in a certain frequency channel. In the illustration, for a frequency channel f1, sound is available from both the first sound source and the second sound source. Therefore, the pulse generator is configured to deliver the stimulation pulses to both the Left CI and Right CI in both first time slot 202 and second time slot 204. However, for frequency channel f2, there is audio content in the sound received from the first sound source and not from the second sound source. Therefore, the stimulation pulse is represented for both Left CI and Right CI but only in the first time slot of the time window. Similarly, if the audio content is only available for the second sound source for a specific frequency channel, then the stimulation pulse is generated and delivered to both Left CI and Right CI but only within the time slot linked to that sound source, as illustrate for frequency channel f3.

RTL and RTR represents the reference times for each time slot, i.e. the starting point of the first time slot and the second time slot. The pulse generator may be configured to provide sound source proximity information with respect a specific CI (either Right CI or Left CI) by utilizing relative timing information for each sound source in relation to respective reference time. The pulse generator is configured to utilize time gap between respective reference time and delivery of respective stimulation pulse in the assigned time slot to represent the proximity. This principle is described earlier with respect to FIG. 4.

The pulse generator is further configured to provide localization information for sound received from a particular sound source by utilizing the disclosed principle of interleaved time slots. For a frequency channel f1, the pulse generator is configured to deliver a first primary stimulation pulse 514 based on the first primary pulse pattern for stimulating, within the first time slot 202, a first cochlea corresponding to the first ear. For example, the first cochlear may correspond to the Left CI having the electrode array (518, FIG. 5). For the same frequency channel f1, the pulse generator is configured to deliver a first secondary stimulation pulse 514' based on the first secondary pulse pattern for stimulating, within the first time slot 202, a second cochlea corresponding to the second ear. For example, the second cochlea may correspond to the Right CI having the electrode array (518', FIG. 5). The first primary stimulation pulse 514 and first secondary stimulation pulse 514' represent a charge amount of FLL and FLR, a difference between the charge amounts represent the primary interaural level difference. Furthermore, the pulse generator is configured to deliver of the first primary stimulation pulse 514 and first secondary stimulation pulse 514' from the reference time RTL of the first time slot 202 such that the difference in delivery, within the first time slot, represents primary interaural time difference ITD.

For the frequency channel f1, the pulse generator is configured to deliver a second primary stimulation pulse 516 based on the second primary pulse pattern for stimulating, within the second time slot 204, a first cochlea corresponding to the first ear. For example, the first cochlear may correspond to the Left CI having the electrode array (518, FIG. 5). For the same frequency channel f1, the pulse generator is configured to deliver a second secondary stimulation pulse 516' based on the second secondary pulse pattern for stimulating, within the second time slot 204, a second cochlea corresponding to the second ear. For example, the second cochlea may correspond to the Right CI having the electrode array (518', FIG. 5). The second primary stimulation pulse 516 and first secondary stimulation pulse 516' represent a charge amounts such that a difference between the charge amounts represent the secondary interaural level difference. Furthermore, the pulse generator is configured to deliver of the second primary stimulation pulse 516 and second secondary stimulation pulse 516' from the reference time RTR of the second time slot 204 such that the difference in delivery, within the second time slot, represents the secondary interaural time difference.

According to an embodiment, the first secondary pulse pattern comprises a copy of the first primary pulse pattern with the primary interaural difference incorporated therein, and the second secondary pulse pattern comprises a copy of the second primary pulse pattern with the secondary interaural difference incorporated therein. Therefore, pulse patterns may be generated based on primary pulse patterns and respective interaural differences.

According to an embodiment, the first secondary pulse pattern comprises the primary interaural difference information and the secondary pulse pattern comprises the secondary interaural difference information. The pulse generator is configured to generate a copy of the first primary pulse pattern, incorporate the primary interaural difference, and generate the first secondary stimulation pulse based on the copy of the first primary pulse pattern incorporating the primary interaural difference. The pulse generator is configured to generate a copy of the second primary pulse pattern, incorporate the secondary interaural difference, and generate the second secondary stimulation pulse based on the copy of the second primary pulse pattern incorporating the secondary interaural difference.

According to an embodiment, the first secondary pulse pattern comprises a copy of the first primary pulse pattern with the primary interaural level difference incorporated therein, and ii) within the first time slot, the processing unit is configured to align transmission of the first primary pulse pattern and first secondary pulse pattern such that a difference between time of arrival of the first primary pulse pattern and time of arrival of the first secondary pulse pattern at the receiver represents the primary interaural time difference. Additionally or alternatively, i) a second secondary pulse pattern comprises a copy of the second primary pulse pattern with the secondary interaural level difference incorporated therein; and ii) within the second time slot, the processing unit is configured to align transmission of the second primary pulse pattern and the second secondary pulse pattern such that a difference between time of arrival of the second primary pulse pattern and time of arrival of the second secondary pulse pattern at the receiver represents the secondary interaural time difference.

According to an embodiment, a primary electrode from a first electrode array implantable in the first cochlea and a secondary electrode from a second electrode array implantable in the second cochlea form the binaural electrode pair. The primary electrode and secondary electrode are defined by the same of overlapping frequency ranges.

In an embodiment, the pulse generator is configured to access the binaural electrode pair information comprising pairing of the primary electrode with the secondary electrode, wherein one electrode of the pair is a master electrode and another electrode is a slave electrode. In different embodiments, accessing the binaural electrode pair information may either be provided as part of the information included in the bit transmitted from the processing unit to the implant or in a look up table. The look up table may typically be stored in a memory of the bilateral cochlear implant system, usually in a memory of the implant. One of the electrode of the binaural pair may be pre-classified or dynamically assigned as the master electrode and another electrode of the binaural pair being pre-classified or dynamically assigned as the slave electrode.

FIG. 8 illustrates a binaural electrode pair between a master electrode and a slave electrode according to an embodiment of the disclosure. For at least frequency channel such as f1; at least one of the first time slot 202 and second time slot 204 includes a first headroom H and a second headroom H' respectively. The first headroom is immediately prior to a first reference time RT comprised within the first time slot 202. Similarly, the second headroom H' is immediately prior to a second reference time comprised within the second time slot.

FIG. 9A illustrates ITD based electrode activation relationship between a master electrode and a slave electrode when ITD=0 according to an embodiment of the disclosure. The illustration only shows the first time slot 202. However, the skilled person would appreciate that the same principle is also applicable to the second time slot as well. In other words, both the primary electrode and the secondary electrode are activated simultaneously. This may happen when the first sound source is not offset with respect to the ears or the horizontal angles at the first ear and the second ear are equal such as the sound coming directly from front or behind.

FIG. 9B illustrates ITD based electrode activation relationship between a master electrode and a slave electrode when ITD=+ve according to an embodiment of the disclosure. The illustration only shows the first time slot 202. However, the skilled person would appreciate that the same principle is also applicable to the second time slot as well. In this embodiment, the master electrode is activated using the first primary stimulation pulse prior to the slave electrode, activated by first secondary stimulation pulse, by ITD/mITD/aITD which is represented by ITD. This may happen when the first sound source is offset such that it is closer to the microphone corresponding to the master electrode.

FIG. 9C illustrates ITD based electrode activation relationship between a master electrode and a slave electrode when ITD=−ve according to an embodiment of the disclosure. The illustration only shows the first time slot 202. However, the skilled person would appreciate that the same principle is also applicable to the second time slot as well. In this embodiment, the master electrode is activated using first primary stimulation pulse at the reference time RT and the slave electrode array is activated using first secondary stimulation pulse prior by ITD to the master electrode, utilizing the headroom H for prior activation.

In the preceding illustrations, P may represent a processing delay prior to each time window such as 202, H represents the first headroom, MSP represents the first primary stimulation pulse for the master electrode, SSP represents the first secondary stimulation pulse for the slave electrode, RT represents the reference time at which master electrode/reassigned master electrode is activated.

According to an embodiment, an electrode of the first electrode array and an electrode of the second electrode array defined by same of substantially overlapping frequency ranges form a binaural electrode pair. One electrode of the pair is pre-classified or dynamically assigned as a master electrode and another electrode as a slave electrode. The pulse generator may be configured to access the binaural electrode pair information, from a memory, comprising pairing of an electrode of an electrode array with an electrode of the another electrode array, wherein one electrode of the pair is a master electrode and another electrode is a slave electrode. At least one of the first time slot includes a first headroom immediately prior to a first reference time comprised within the first time slot and the second time slot includes a second headroom immediately prior to a second reference time comprised within the second time slot. For each time slot, the pulse generator is configured to specify the interaural time difference relative to the master electrode such that when the interaural time difference is positive, the master electrode is activated at a reference time prior to the slave electrode. For each time slot, the pulse generator is configured to specify the interaural time difference relative to the master electrode such that when the interaural time difference is negative, i) the slave electrode is activated prior to the master electrode such that the master electrode is activated at the first reference time and the slave electrode is activated utilizing the first headroom for stimulation based on the first primary stimulation pulse and first secondary stimulation pulse and ii) the slave electrode is activated prior to the master electrode such that the master electrode is activated at the second reference time and the slave electrode is activated utilizing the second headroom for stimulation based on the second primary stimulation pulse and second secondary stimulation pulse. Alternatively, for each time slot, the pulse generator is configured to specify the interaural time difference relative to the master electrode such that when the interaural time difference is negative, the master electrode is reassigned as a slave electrode and the slave electrode is reassigned as a master electrode, such that the reassigned master electrode is activated at the reference time and prior to the reassigned slave electrode without need of the headroom.

According to an embodiment, the processing unit is configured to control transmission rate of the pulse patterns from the transmitter to receiver such that the primary pulse pattern and the secondary pulse pattern, or the first pulse pattern and second pulse pattern are transmitted sequentially within the time window comprising the first slot and second slot.

FIG. 10 illustrates stimulation rate in accordance with determined frequency band according to an embodiment of the disclosure. The processing unit is configured to determine whether the first band and second band include low frequencies or high frequencies. In another embodiment, the processing unit is configured to determine whether at least one of i) the first primary band limited signal, and first secondary band limited signal, and ii) the second primary band limited signal and a second secondary band limited signal include low frequencies or high frequencies. The processing unit is configured to generate stimulation pulse patterns corresponding to at least one of i) both the first band and second band, ii) both the first primary band limited signal, and first secondary band limited signal, and iii) both the second primary band limited signal and a second secondary band limited signal at a generation rate that is same as the frame rate in response to identification of the band(s)/band limited signal(s) include high frequencies. The processing unit is configured to generate stimulation pulse patterns corresponding to at least one of i) both the first band and second band, ii) both the first primary band limited signal, and first secondary band limited signal, and iii) both the second primary band limited signal and a second secondary band limited signal at a generation rate that is lower than a frame rate in response to identification of the band(s)/band limited signal(s) and second band include low frequencies. Thus, the implant is configured to generate and deliver stimulation pulses based on the generated stimulation pulse patterns in all time frames for high frequencies and only in a few time frames for low frequencies. For example, f1 represents the frequency channel associated with the low frequency band such as 100 Hz-200 Hz and f5 represents the frequency channel associated with the high frequency band such as 2800 Hz-3500 Hz. If the generation rate for low frequency band is 100 Hz and the generation rate for high frequency band is 1000 Hz, then the generation rate for generating stimulation pulse patterns for high frequencies is 10 times than the generation rate for generating stimulation pulse patterns of low frequencies. In other words, the stimulation pulse corresponding to stimulation pulse pattern for high frequencies is generated for each of 10 time frames, i.e. for each of Frame 1 through Fr 10 and the stimulation pulse corresponding to stimulation pulse patterns for low frequencies is generated only once per 10 time frames, i.e. in Frame 1 for time frames from Frame 1 through Fr 10. This stimulation may be repeated in same fashion, i.e generating stimulation pulse once for low frequency in Frame 11 from Frame 11 through to Frame 20, whereas stimulation pulse is generated for high frequencies for each time frame from Frame 11 through to Frame 20. 208 represents time frame 1, 208" represents time frame 11, 206 and 206" represents time windows corresponding to frequency channel f1 (corresponding to low frequencies) in frame 1 and frame 11 respectively, 202 and 202", and 204 and 204" represent first time slot and second time slot in time frame 1 and time frame 11 respectively, 1006 and 1006" represent time windows corresponding to frequency channel f5 (corresponding to high frequencies) in frame 1 and frame 11 respectively, 1002 and 1002", and 1004 and 1004" represent first time slot and second time slot corresponding to f5 in time frame 1 and time frame 11 respectively, and Fr 2, . . . Fr 10 represents time frames from time frame 2 through time frame 10.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

Accordingly, the scope should be judged in terms of the claims that follow.

The invention claimed is:

1. A cochlear implant system comprising
an external part, configured to sit behind one of the user's ears, in which are arranged
   an input unit comprised of a microphone array, said input unit being configured to provide a first electrical signal from a first sound source and a second electrical signal from a second sound source, said microphone array being configured to utilize a beamforming algorithm to steer a listening beam toward the first sound source while still receiving sound from the second sound source,
   a filterbank configured to filter the first electrical signal into a plurality of first band limited signals and the second electrical signal into a plurality of second band limited signals, and
   a processing unit configured to generate a primary pulse pattern based on a first band selected from the plurality of first band limited signals and to generate a secondary pulse pattern based on a second band selected from the plurality of second band limited signals, the first band and the second band being defined by same or substantially overlapping frequency ranges; and
an implant configured to receive the primary pulse pattern and the secondary pulse pattern from the processing unit, wherein
   the primary pulse pattern is configured to stimulate a cochlea of a user of the cochlear implant system during a first time slot, and
   the secondary pulse pattern is configured to stimulate the cochlea of the user of the cochlear implant system during a second time slot, and
   the first time slot and the second time slot are sequential time slots.

2. The cochlear implant system according to claim 1, wherein the first time slot and the second time slot are sequentially comprised in a time window transferred from the processing unit to the implant, wherein
   the time window corresponds to a predefined time duration commonly represented by each of the first and second time slots, during which an electrode of an electrode array implantable in the cochlea is configured to stimulate an auditory nerve based on the first and second sound sources, the electrode being associated with a specific frequency channel corresponding to the first band and second band,
   the starting point of the first time slot in the time window and the starting point of the second time slot within the time window are reference times commonly representing the start of the predefined time duration, such that proximities of the first and second sound sources are indicated by relative timings of the primary and secondary pulse patterns in relation to the reference times of the first and second time slots, respectively.

3. The cochlear implant system according to claim 2, wherein
   a plurality of time windows are comprised in a time frame during which one cycle of stimulation at the cochlea is completed,
   each time window of the plurality of time windows corresponds to a specific frequency channel assigned to a specific electrode of the electrode array,
   each time window comprises sequential first and second time slots during which stimulation corresponding to the first sound source and second sound source for the specific frequency channel is sequentially provided such that the first and second time slots across the time windows are provided in an interleaved manner, and
   the time frame is followed by a subsequent time frame during which a subsequent cycle of stimulation at the cochlea is completed.

4. The cochlear implant system according to claim 3, wherein the microphone array is configured to receive a mixed electrical signal from the first sound source and the second sound source; and
   the system further comprising a resolution unit that is configured to unmix the mixed electrical signal into the first electrical signal and the second electrical signal.

5. The cochlear implant system according to claim 2, wherein
   a plurality of time windows are comprised in a time frame during which one cycle of stimulation at the cochlea is completed,
   each time window of the plurality of time windows corresponds to a specific frequency channel assigned to a specific electrode of the electrode array,
   each time window comprises sequential time slots during which stimulation corresponding to the first sound source and second sound source for the specific frequency channel is sequentially provided such that the time slots across the time windows are provided in an interleaved manner, and
   the time frame is followed by a subsequent time frame during which a subsequent cycle of stimulation at the cochlea is completed.

6. The cochlear implant system according to claim 2, wherein the microphone array is configured to receive a mixed electrical signal from the first sound source and the second sound source; and
   the system further comprising a resolution unit that is configured to unmix the mixed electrical signal into the first electrical signal and the second electrical signal.

7. The cochlear implant system according to claim 1, wherein the microphone array is configured to receive a mixed electrical signal from the first sound source and the second sound source; and
   the system further comprising a resolution unit that is configured to unmix the mixed electrical signal into the first electrical signal and the second electrical signal.

8. The cochlear implant system according to claim 1, wherein the processing unit is configured to control transmission rate of the pulse patterns from the transmitter to receiver such that the primary pulse pattern and the secondary pulse pattern, or the first pulse pattern and second pulse pattern are transmitted sequentially within the time window comprising the first slot and second slot.

9. The cochlear implant system according to claim 1, wherein the processing unit is configured to
   determine whether at least one of the i) first band and second band, ii) the first primary band limited signal, and first secondary band limited signal, and iii) the second primary band limited signal and second secondary band limited signal include low frequencies;
   generate stimulation pulse patterns corresponding to at least one of i) both the first band and second band, ii) both the first primary band limited signal, and first secondary band limited signal, and iii) both the second primary band limited signal and a second secondary band limited signal at a generation rate that is lower than a frame rate in response to identification of the band(s)/band limited signal(s) and second band include low frequencies.

10. A bilateral cochlear implant system comprising
   a first microphone array configured to be positioned at or in vicinity of a first ear of the user, the first microphone array being configured to utilize a beamforming algorithm to steer a listening beam and generate a first electrical signal in response to receiving a sound from at least one sound source;
   a second microphone array configured to be positioned at or vicinity of a second ear of the user, the second microphone array being configured to utilize a beamforming algorithm to steer a listening beam and generate a second electrical signal in response to receiving the sound from the at least one sound source;
   a common filterbank receiving the first and second electrical signals from the first and second microphone arrays, respectively, the filterbank being further configured to filter the first electrical signal into a plurality of first band limited signals and to filter the second electrical signal into a plurality of second band limited signals;
   a processing unit configured to generate
      a first pulse pattern comprising i) a first primary pulse pattern based on a first band selected from the plurality of first band limited signals into which the first electric signal is filtered, and ii) a first secondary pulse pattern based on a first band selected from the plurality of second band limited signals into which the second electric signal is filtered, corresponding to the first secondary signal, and
      a second pulse pattern comprising i) a second primary pulse pattern based on a second band selected from the plurality of first band limited signals into which the first electrical signal is filtered, and ii) a second secondary pulse pattern based on a second band selected from the plurality of second band limited signals into which the second electric signal is filtered;
   the implant comprising
   first and second electrode arrays configured to be implanted in first and second *cochleae* corresponding to the first and second ears of the user, respectively, wherein the first electrode array is configured to
      i) use a first primary stimulation pulse generated based on the first primary pulse pattern for stimulating, within the first time slot, a first cochlea corresponding to the first ear, and ii) use a second primary stimulation pulse generated based on the second primary pulse pattern for stimulating, within the second time slot, the first cochlea corresponding to the second ear, and
   wherein the second electrode array is configured to
   receive the first secondary pulse pattern and the second secondary pulse pattern from the processing unit, and i) use a first secondary stimulation pulse generated based on the first secondary pulse pattern for stimulating, within the first time slot, the second cochlea corresponding to the first ear, and ii) use a second secondary stimulation pulse generated based on the second secondary pulse pattern for stimulating, within the second time slot, the second cochlea corresponding to the second ear.

11. The cochlear implant system according to claim 10, wherein the first time slot and the second time slot are sequentially comprised in a time window transferred from the processing unit to the implant, wherein
   the time window corresponds to a predefined time duration commonly represented by each of the first and second time slots, during which stimulation for a specific frequency channel, defined by the corresponding bands, using the first electrode array implantable in the first cochlea for stimulating the first cochlea and the second electrode array implantable in the second cochlea for stimulating the second cochlea is provided,
   the stimulation for the specific frequency channel corresponds to sounds from first and second sound sources, respectively, and
   the starting point of the first time slot in the time window and the starting point of the second time slot within the time window are reference times commonly representing the start of the predefined time duration, such that proximities of the first and second sound sources are indicated by relative timings of primary and secondary pulse patterns in relation to the reference times of the first and second time slots, respectively.

12. The bilateral cochlear implant system according to claim 11, wherein
   the first microphone array is configured to generate the first electrical signal as a first mixed electrical signal in which the sound from the first sound source and the sound from the second sound source are mixed;
   the second microphone array is configured to generate the second electrical signal as a second mixed electrical signal in which the sound from the first sound source and the sound from the second sound source are mixed; and
   the bilateral cochlear implant system further comprises
      a resolution unit configured to unmix the first mixed electrical signal into a first primary signal and a second primary signal and to unmix the second mixed electrical signal into first secondary signal and a second secondary signal, the first primary signal and the second primary signal corresponding to the sound received from the first sound source at the first microphone and the second microphone respectively and the first secondary signal and the second secondary signal corresponding to the sound received from the second sound source at the first microphone array and the second microphone array respectively, and
      a pulse generator configured to generate
      i) the first primary stimulation pulse based on the first primary pulse pattern, the first primary stimulation pulse being used by the first electrode array for stimulating, within the first time slot, the first cochlea corresponding to the first ear, and ii) a first secondary stimulation pulse based on the first secondary pulse pattern, the first secondary stimulation pulse being used by the second electrode array for stimulating, within the first time slot, the second cochlea corresponding to the second ear, and i) the second primary stimulation pulse based on the second primary pulse pattern, the second primary stimulation pulse being used by the first electrode array for stimulating, within the second time slot, the first cochlea corresponding to the first ear, and ii) a second secondary stimulation pulse based on the second secondary pulse pattern, the second secondary stimulation pulse being used by the second electrode array for stimulating, within the second time slot, the second cochlea corresponding to the second ear.

13. The cochlear implant system according to claim 12, wherein the filterbank is configured to filter the first primary signal into a plurality of first primary band limited signals, the first secondary signal into a plurality of first secondary band limited signals, the second primary electrical signal into a plurality of second primary band limited signals and the second secondary signal into a plurality of second secondary band limited signals; and the first pulse pattern and second pulse pattern are generated for corresponding bands, defined by same or substantially overlapping frequency ranges, selected from the plurality of first primary band limited signals, plurality of first secondary band limited signals, plurality of second primary band limited signals, and plurality of second secondary band limited signals respectively.

14. The cochlear implant system according to claim 12, further comprising a transmitter configured to transmit i) the first pulse pattern and the second pulse pattern from the processing unit to the pulse generator within the time window, or ii) alternatively transmit the first pulse pattern in the first time slot and the second pulse pattern in the second time slot from the processing unit to the pulse generator; and a receiver configured to receive the first pulse pattern and the second pulse pattern within the time window, or ii) alternatively receive the first pulse pattern in the first time slot and the second pulse pattern in the second time slot.

15. The cochlear implant system according to claim 12, wherein the first secondary pulse pattern comprises a copy of the first primary pulse pattern with a primary interaural difference incorporated therein, and the second secondary pulse pattern comprises a copy of the second primary pulse pattern with a secondary interaural difference incorporated therein.

16. The cochlear implant system according to claim 12, wherein the first secondary pulse pattern comprises a primary interaural difference information and the secondary pulse pattern comprises a secondary interaural difference information; and the pulse generator is configured to generate a copy of the first primary pulse pattern, incorporate the primary interaural difference, and generate the first secondary stimulation pulse based on the copy of the first primary pulse pattern incorporating the primary interaural difference, and generate a copy of the second primary pulse pattern, incorporate the secondary interaural difference, and generate the second secondary stimulation pulse based on the copy of the second primary pulse pattern incorporating the secondary interaural difference.

17. The cochlear implant system according to claim 12, wherein i) the first secondary pulse pattern comprises a copy of the first primary pulse pattern with a primary interaural level difference incorporated therein, and ii) within the first time slot, the processing unit is configured to align transmission of the first primary pulse pattern and first secondary pulse pattern such that a difference between time of arrival of the first primary pulse pattern and time of arrival of the first secondary pulse pattern at the receiver represents a primary interaural time difference; and/or i) a second secondary pulse pattern comprises a copy of the second primary pulse pattern with a secondary interaural level difference incorporated therein; and ii) within the second time slot, the processing unit is configured to align transmission of the second primary pulse pattern and the second secondary pulse pattern such that a difference between time of arrival of the second primary pulse pattern and time of arrival of the second secondary pulse pattern at the receiver represents a secondary interaural time difference.

18. The cochlear implant system according to claim 12, wherein a plurality of time windows are comprised in a time frame during which one cycle of auditory nerve stimulation at the first cochlea and the second cochlea is completed, each time window of the plurality of time windows corresponds to a specific frequency channel assigned to a specific binaural electrode pair comprising pairing of an electrode of first electrode array with an electrode of the second electrode array, each time window comprises sequential time slots during which stimulation corresponding to the first sound source and second sound source for the specific frequency channel is sequentially provided such that the time slots across the time windows are provided in an interleaved manner, and the time frame is followed by a subsequent time frame during which a subsequent cycle of the auditory nerve stimulation at the first cochlea and the second cochlea is completed.

19. The cochlear implant system according to claim 12, wherein an electrode of the first electrode array and an electrode of the second electrode array defined by same of substantially overlapping frequency ranges form a binaural electrode pair, one electrode of the pair being pre-classified or dynamically assigned as a master electrode and another electrode as a slave electrode;

at least one of the first time slot comprising a first headroom immediately prior to a first reference time comprised within the first time slot and the second time slot comprising a second headroom immediately prior to a second reference time comprised within the second time slot;

for each time slot, the pulse generator is configured to specify the interaural time difference relative to the master electrode such that when the interaural time difference is positive, the master electrode is activated at a reference time prior to the slave electrode, and specify the interaural time difference relative to the master electrode such that when the interaural time difference is negative, i) the slave electrode is activated prior to the master electrode such that the master electrode is activated at the first reference time and the slave electrode is activated utilizing the first headroom for stimulation based on the first primary stimulation pulse and first secondary stimulation pulse and ii) the slave electrode is activated prior to the master electrode such that the master electrode is activated at the second reference time and the slave electrode is activated utilizing the second headroom for stimulation based on the second primary stimulation pulse and second secondary stimulation pulse; or the master electrode is reassigned as a slave electrode and the slave electrode is reassigned as a master electrode, such that the reassigned master electrode is activated at the reference time and prior to the reassigned slave electrode without need of the headroom.

\* \* \* \* \*